US009133578B2

(12) United States Patent
Ruda et al.

(10) Patent No.: US 9,133,578 B2
(45) Date of Patent: Sep. 15, 2015

(54) POLYMER MADE OF A PRIMARY AMINE FUNCTIONALIZED POLYMER AND A HEMICELLULOSE

(75) Inventors: Marcus Ruda, Bandhagen (SE); Rikard Slättegård, Solna (SE)

(73) Assignee: CELLUTECH AB, Stockholm (SE)

( * ) Notice: Subject to any disclaimer, the term of this patent is extended or adjusted under 35 U.S.C. 154(b) by 0 days.

(21) Appl. No.: 13/319,329

(22) PCT Filed: May 27, 2010

(86) PCT No.: PCT/SE2010/050570
§ 371 (c)(1),
(2), (4) Date: Nov. 7, 2011

(87) PCT Pub. No.: WO2010/138069
PCT Pub. Date: Dec. 2, 2010

(65) Prior Publication Data
US 2012/0058536 A1    Mar. 8, 2012

Related U.S. Application Data

(60) Provisional application No. 61/181,303, filed on May 27, 2009.

(30) Foreign Application Priority Data

May 27, 2009    (SE) ...................................... 0950378

(51) Int. Cl.
| C08B 37/14 | (2006.01) |
| D21H 17/24 | (2006.01) |
| C08L 5/14 | (2006.01) |
| D06M 15/03 | (2006.01) |
| C08B 37/00 | (2006.01) |
| C08L 97/02 | (2006.01) |
| C09D 105/00 | (2006.01) |
| C11D 3/22 | (2006.01) |
| C11D 3/37 | (2006.01) |
| D21H 17/56 | (2006.01) |
| D21H 21/28 | (2006.01) |
| C08G 81/00 | (2006.01) |
| C08G 81/02 | (2006.01) |
| C08L 1/02 | (2006.01) |

(52) U.S. Cl.
CPC ........... *D06M 15/03* (2013.01); *C08B 37/0057* (2013.01); *C08G 81/00* (2013.01); *C08G 81/02* (2013.01); *C08L 97/02* (2013.01); *C09D 105/00* (2013.01); *C11D 3/227* (2013.01); *C11D 3/3723* (2013.01); *C11D 3/3769* (2013.01); *D21H 17/24* (2013.01); *D21H 17/56* (2013.01); *D21H 21/28* (2013.01)

(58) Field of Classification Search
CPC ....... C08B 37/0057; D21H 17/24; C08L 5/14
See application file for complete search history.

(56) References Cited

U.S. PATENT DOCUMENTS

| 4,976,952 A * | 12/1990 | Lang et al. ...................... 424/47 |
| 6,331,607 B1 | 12/2001 | Bohlander et al. |
| 6,756,363 B1 * | 6/2004 | Nordquist et al. .............. 514/55 |
| 2004/0192646 A1 | 9/2004 | Yura et al. |

FOREIGN PATENT DOCUMENTS

| CN | 101240087 A | 8/2008 |
| EP | 1897893 A1 | 3/2008 |
| JP | 5-140213 A | 6/1993 |
| JP | 11-180813 A | 7/1999 |
| JP | 2009-227887 A | 10/2009 |
| JP | 2012-512268 A | 5/2012 |
| WO | 99/01479 A1 | 1/1999 |
| WO | 99/36469 A1 | 7/1999 |
| WO | 00/27889 A1 | 5/2000 |
| WO | 00/65014 A1 | 11/2000 |
| WO | 2006/092057 A1 | 9/2006 |
| WO | WO-2010/070655 | 6/2010 |

OTHER PUBLICATIONS

Umemura et al., J. Appl. Poly. Sci., 2008, 108, p. 2481-2487, published online Feb. 20, 2008.*
Kato et al., J. Agric. Food. Chem., 1993, 41, p. 540-543.*
Janciauskaite et al., "Synthesis and Study of Chitosans with Linear Oligosaccharide Branches", Proceedings of Baltic Polymer Symposium 2007, Sep. 19-21, 2007, 8 pages.
Daus et al., "Towards Unnatural Xylan Based Polysaccharides: Reductive Amination as a Tool to Access Highly Engineered Carbohydrates", Cellulose, vol. 17, 2010, pp. 825-833.
Shaath, Nadim A., "Encyclopedia of UV Absorbers for Sunscreen Products", Cosmetics & Toiletries, vol. 102, Mar. 1987, pp. 21-39.
Wagner et al., "Silicon-Modified Carbohydrate Surfactants III: Cationic and Anionic Compounds", Applied Organometallic Chemistry, vol. 11, 1997, pp. 523-538.
International Preliminary Report on Patentability received for PCT Patent Application No. PCT/SE2010/050570, issued on Nov. 29, 2011, 10 pages.
International Search Report and Written Opinion received for PCT Patent Application No. PCT/SE2010/050570, mailed on Sep. 14, 2010, 14 pages.
Extended European Search Report received for European Patent Application No. 10780890.9, mailed on May 7, 2013, 4 pages.
Gabrielii et al., "Preparation and Properties of Hydrogels Based on Hemicellulose", Journal of Applied Polymer Science, vol. 69, 1998, pp. 1661-1667.

(Continued)

*Primary Examiner* — Shaojia Anna Jiang
*Assistant Examiner* — Jonathan S Lau
(74) *Attorney, Agent, or Firm* — Morrison & Foerster LLP

(57) ABSTRACT

The present invention relates to a polymer made of a primary amine functionalized polymer and a hemicellulose e.g. chitosan and xyloglucan, wherein the primary amine functionalized polymer is covalently bound to the hemicellulose, and to a cross-linking agent composition comprising the polymer. A method wherein manufacturing a cellulose containing product comprises the steps of; providing a cellulose containing product; treating said cellulose product with a cellulose adsorbing agent comprising a polymer made of a primary amine functionalized polymer and a hemicellulose e.g. chitosan and xyloglucan, and optionally other additives is also provided.

18 Claims, 21 Drawing Sheets

(56) References Cited

OTHER PUBLICATIONS

Matsuda et al., "Chemoenzymatic Synthesis of Amylose-Grafted Chitosan", Macromolecular Rapid Communications, vol. 28, 2007, pp. 863-867.
Office Action received for Chinese Patent Application No. 201080023006.0, mailed on Sep. 4, 2013, 23 pages (14 pages of English Translation and 9 pages of Official copy).
Janciauskaite et al., "Synthesis and Properties of Chitosan-N-Dextran Graft Copolymers", Reactive & Functional Polymers, vol. 68, 2008, pp. 787-796.
Office Action Received for Chinese Patent Application No. 201080023006.0, mailed on Apr. 23, 2014, 16 pages (5 pages of English Translation and 11 pages of Official copy).
Li, "The Interface Behavior and Application of Chitosan and its Ionic Derivative as Wet-End additives in Papermaking Systems", Nov. 15, 2006, 8 pages. See statement under 37 CFR § 1.98(a) (3).
Sang et al., "Preparation and Application of Chitosan's Derivatives as a Multifunctional Chemical in Papermaking Industry", Feb. 15, 2007, 4 pages. See statement under 37 CFR § 1.98(a) (3).
Qiang et al., "Application of Chitosan and Derivative in Paper-Making Industry", Tianjin University of Science and Technology, Jun. 15, 2003, pp. 12-13 (English Abstract only). See statement under 37 CFR § 1.98(a) (3).
Office Action received for Japanese Patent Application No. 2012-513015, issued on Feb. 4, 2014, 10 pages (5 pages of English Translation and 5 pages of Official Copy).
Chinese Office Action dated Oct. 22, 2014, for CN Application No. 201080023006, 28 pages (English translation attached, 21 pages).
European Office Action dated Feb. 11, 2014, for EP Application No. 10780890, 6 pages.
European Office Action dated Jun. 25, 2014, for EP Application No. 10780890, 4 pages.
Japanese Office Action dated Jul. 22, 2014, for JP Application No. 2012-513015, 5 pages (English translation attached, 5 pages).
Rinaudo et al. (2010). "New way to crosslink chitosan in aqueous solution," European Polymer Journal 46(7):1537-1544.
Wang (1997). "Production process of beer," China Light Industrial Press, 1st edition, p. 24 (partial English translation attached, 1 page).
Yu et al. (2007). "Preparation and properties of novel hydrogels from oxidized konjac glucomannan cross-linked chitosan for invitro drug delivery," Macromolecular Bioscience 7(9-10):1100-1111.

* cited by examiner

US 9,133,578 B2

POLYMER MADE OF A PRIMARY AMINE FUNCTIONALIZED POLYMER AND A HEMICELLULOSE

CROSS REFERENCE TO RELATED APPLICATIONS

This is a U.S. National Phase patent application of PCT/SE2010/050570, filed May 27, 2010, which claims priority to the Swedish Patent Application No. 0950378-0, filed May 27, 2009, and the U.S. Provisional Patent Application No. 61/181,303, filed May 27, 2009, each of which is hereby incorporated by reference in the present disclosure in its entirety.

TECHNICAL FIELD

The present invention relates to a chemical product, which can be used as cross-linking agent and/or a cellulose adsorbing agent in the manufacture of paper products or textile products. A cellulose adsorbing agent is an agent that is adsorbed to cellulose, in the manufacture of or in the treatment of cellulose products, which will get improved physical properties e.g. tensile strength, strain at break, tensile energy absorption, tear index, and folding endurance (double fold). The invention also relates to a cross-linking agent composition and/or a cellulose adsorbing agent composition, and a cellulose product such as paper, textile or paperboard product comprising said chemical product, a method of manufacturing said cellulose product and a use of said chemical product.

BACKGROUND

In the manufacture of cellulose products such as paper and paperboard products various additives are used to improve the properties of the product. Cross-linking agents are used to improve the strength of paper products. There is still a need to provide stronger paper products.

Chitosan has been used as additive in the manufacture of paper products. A drawback with chitosan is its low solvability in non-acidic water.

Xyloglucan is adsorbing very slowly and poorly to textiles.

Furthermore, cellulose is the major raw material in other industries such as the textile industry. In spinning and in weaving mills there is a need for stronger threads.

In some use of woven textiles there is need for improved properties, such properties can be fire resistance, biocidal properties such as antibacterial and antifungal properties.

In cleaning of cellulose containing material, such as textiles of different kind there is a need of improved laundry and cleaning properties.

In summary, there is a strong need for methods and chemical compounds/products that will improve cellulose based products.

SUMMARY OF THE INVENTION

The object of the present invention is to provide a chemical product, which can be used as a cellulose adsorbing agent or a cross-linking agent in the manufacture of cellulose products, having for example improved folding endurance, improved tensile index, tensile stiffness, tensile energy absorption, strain at break, modulus of elasticity or wet strength properties, or in modifying cellulose products in order to get a desired property of the cellulose product.

This object is achieved according to the present invention by the provision of a polymer made of primary amine functionalized polymer and hemicellulose, wherein the primary amine functionalized polymer is covalently bound to the hemicellulose.

The primary amine functionalized polymer and hemicellulose may be bound to each other by reductive amination between free amino groups of the primary amine functionalized polymer and a reducing end of hemicellulose.

An additional object is to provide a cellulose containing product comprising a polymer made of primary amine functionalized polymer and hemicellulose, wherein the primary amine functionalized polymer is covalently bound to the hemicellulose. The cellulose containing product may be a paper, paperboard, filter papers, fine papers, banknote paper, newsprint, liner boards, tissue and other hygiene products, sack, kraft papers, textile, cardboards, a thread such as a cotton thread, woven or non-woven fabric, wood product, pulp, cellulosic membranes, cotton product, linen product, hemp product, flax product, viscose product, product of regenerated cellulose, ramie product, bacterial cellulose product, cellulose product or any other non-wood based cellulose product.

Further, the cellulose in the cellulose containing product may originate from wood, plant, cotton, or any other non-wood based cellulose, linen, hemp, flax, viscose, regenerated cellulose, product of cellulose derivatives, ramie, bacterial cellulose, and mixtures thereof.

In addition, the cellulose in the cellulose containing product may originate from a mix of different plants.

The present invention also provides the use of a polymer as a cross-linking agent and/or a cellulose adsorbing agent.

An object is achieved according to the present invention by the provision of a water soluble material made of chitosan and xyloglucan. The present invention thus relates to a water soluble material made of chitosan and xyloglucan wherein chitosan is covalently bound to xyloglucan.

BRIEF DESCRIPTION OF THE DRAWINGS

The invention is described together with the following figures.

DETAILED DESCRIPTION

Figure 1A:
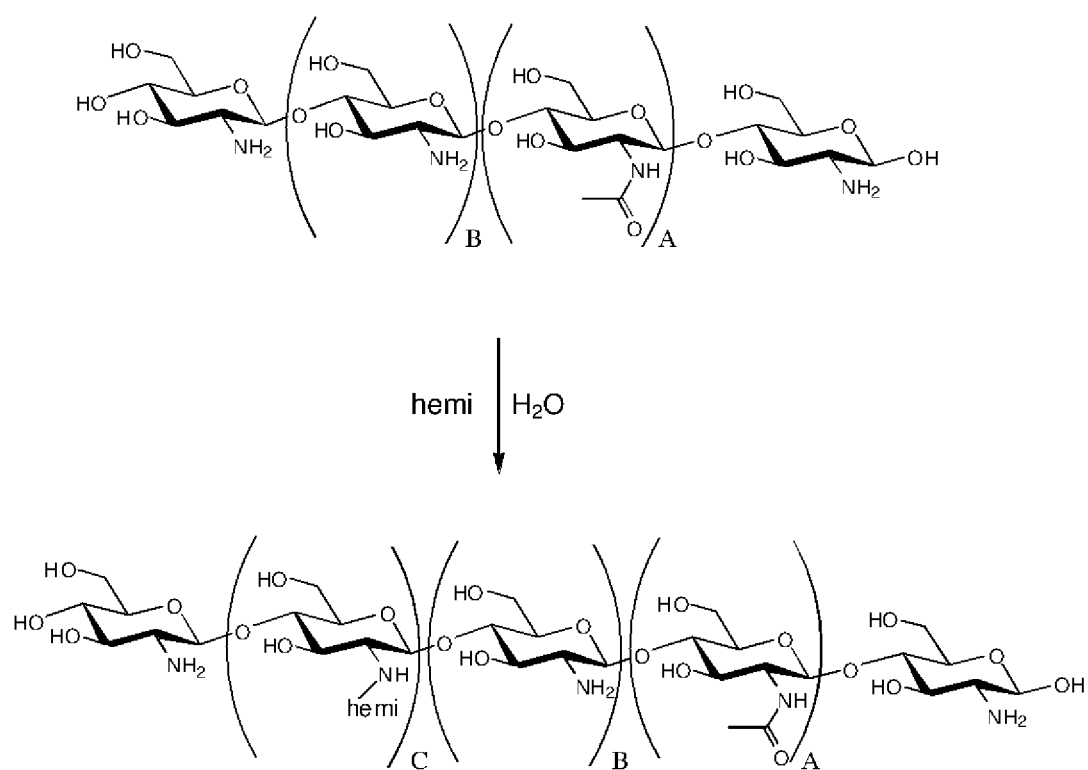
FIG. 1a Show the synthesis of the polymer made of chitosan and a hemicellulose. Chitosan reacting with hemicellulose (hemi) resulting in a hemicellulose modified chitosan.

The present invention relates to a polymer made of a primary amine functionalized polymer and a hemicellulose, wherein the primary amine functionalized polymer is covalently bound to the hemicellulose. The inventors have found that it is possible to produce a polymer from a primary amine functionalized polymer and a hemicellulose. This polymer has very good effects when used in cellulose products. The polymer is adsorbed very effective to cellulose products and it also works as a cross-linking agent. The polymer may then be a cross-linking agent and/or a cellulose adsorbing agent, since it can both adsorb to a cellulose product and work as a cross-linking agent in cellulose at the same time. The invention also relates to a cross-linking agent composition comprising the polymer made of a primary amine functionalized polymer and a hemicellulose. The polymer can also be considered to modify a cellulose product. Thus, the polymer can be considered as a modifying agent. The primary amine functionalized polymer may be covalently bound to the reducing end of the hemicellulose.

Further, the present invention relates to a polymer, wherein the primary amine functionalized polymer and the hemicellulose are bound to each other by reductive amination between free amino groups of the primary amine functionalized polymer and the reducing end of the hemicellulose. This is a suitable and effective way of producing the polymer according to the present invention.

The present invention also relates to a polymer, wherein the primary amine functionalized polymer and the hemicellulose are bound to each other by an imine bond between the amino groups of the primary amine functionalized polymer and the reducing end of the hemicellulose. This is an alternative way of producing the material compared to reductive amination which is described above.

A hemicellulose can be any of several heteropolymers present in almost all plant cell walls e.g. xylan, arabinoxylan, glucuronoxylan, glucuronoarabinoxylan, glucomannan, galactomannan, galactoglucomannan, and xyloglucan. Hemicellulose contains many different sugar monomers. Any molecular weight of the hemicellulose can be used in the present invention.

The hemicellulose may be selected from the group comprising xylan, arabinoxylan, glucuronoxylan, glucuronoarabinoxylan, glucomannan, galactomannan, galactoglucomannan, and xyloglucan or a combination thereof.

The main chain of xylan is composed of $\beta$-(1→4)-linked D-xylopyranose residues. Besides xylose, xylans may contain arabinose, glucuronic acid or its 4-O-methyl ether, and acetic, ferulic, and p-coumaric acids. The frequency and composition of branches are dependent on the source of the xylan. All types of xylan may be used according to the invention.

Galactomannans are polysaccharides consisting of $\beta$-(1→4)-linked D-mannopyranose backbone with branch-points from their 6-positions linked to $\alpha$-D-galactose. All types of galactomannan may be used according to the invention. The ratio between mannose and galactose may be different as described below for different natural gums.

fenugreek gum, mannose:galactose ~1:1
guar gum, mannose:galactose ~2:1
tara gum, mannose:galactose ~3:1
locust bean gum or carob gum, mannose:galactose ~4:1

Glucomannan is mainly a straight-chain polymer, with a small amount of branching. The component sugars are $\beta$-(1→4)-linked D-mannose and D-glucose in a ratio of 1.6:1. Glucomannan comprises 40% by dry weight of the roots or corm of the konjac plant. All types of glucomannan may be used according to the invention.

Galactoglucomannan is a water-soluble hemicellulose, consisting of galactose, glucose and mannose. Many softwood species, e.g. Norway spruce are rich of galactoglucomannans and can contain it up to 10-20%. Galactoglucomannan consists of a backbone of randomly distributed $\beta$-(1→4)-linked mannose and glucose units with $\alpha$-(1→6)-linked galactose units attached to mannose units. The hydroxyl groups in locations C2 and C3 in mannose are partially substituted by acetyl groups. All types of galactoglucomannan may be used according to the invention.

Xyloglucan has a backbone of $\beta$-(1→4)-linked glucose residues most of which are substituted with $\alpha$-(1→6)-linked xylose side chains. The xylose residues are often capped with a galactose residue or sometimes followed by a fucose or an arabinose residue. The specific structure of xyloglucan varies among plant families. All types of xyloglucans may be used according to the invention.

A primary amine functionalized polymer is a polymer that has primary amines. Any kind of structure and molecular weight of the polymer can be used in the present invention e.g. linear polymers, star polymers, comb polymers, brush polymers, dendronized polymers, ladders, dendrimers, and co-polymers. Examples of commercial primary amine functionalized polymers are homopolymer or co-polymers containing e.g. polyallylamine, polyvinylamine, poly(vinylamine-co-vinylformamide), poly(ethyleneimine), and chitosan.

According to the present invention, the primary amine functionalized polymer may be selected from the group of homo- or co-polymers comprising comprising polyallylamine, polyvinylamine, poly(vinylamine-co-vinylformamide), poly(ethyleneimine), and chitosan or a combination thereof. The primary amine functionalized polymer may also be selected from the group comprising polyallylamine, polyvinylamine, poly(vinylamine-co-vinylformamide), poly(ethyleneimine), and chitosan or a combination thereof. There exist a wide variety of chitosans, and any chitosan may be used. A synthesis of making a polymer of polyallylamine is disclosed in FIG. 1c. In FIG. 1d a synthesis of making a polymer of polyvinylamine is disclosed. In FIG. 1e one example of the synthesis of a polymer made of polyethyleneimine and hemicellulose is disclosed.

The polymer may be made of any combination of the hemicelluloses above and the primary functionalized polymers above.

The hemicellulose may have a molecular weight of 180 Da to more than 2000 kDa. Further, the hemicellulose may have the molecular weight of 180 Da-20 kDa, 180 Da-100 kDa, 180 Da-500 kDa, 180 Da-1000 kDa, 180 Da-2000 kDa 180 Da to more than 2000 kDa, 1 kDa-2000 kDa, 10 kDa-2000 kDa, 20 kDa-2000 kDa, 50 kDa-2000 kDa, 100 kDa-2000 kDa, 500 kDa-2000 kDa, 10 kDa to more than 2000 kDa, or 20 kDa to more than 2000 kDa in the present invention.

The primary amine functionalized polymer may have a molecular weight of 100 Da to more than 1000 kDa. Further, the primary amine functionalized polymer can have a molecular weight of 100 Da-20 kDa, 100 Da-100 kDa, 100 Da-500 kDa, 100 Da-1000 kDa, 100 Da to more than 1000 kDa, 1 kDa-1000 kDa, 10 kDa-1000 kDa, 20 kDa-1000 kDa, 50 kDa-1000 kDa, 100 kDa to 1000 kDa, 500 kDa-1000 kDa, 10 kDa to more than 1000 kDa, or 20 kDa to more than 1000 kDa in the present invention The polymer is usually a water soluble material. However, it is not always water soluble. It may depend on the pH of the solution.

Further, the polymer may not be water soluble.

An example of a polymer made of primary amine functionalized polymer and hemicellulose e.g. chitosan and hemicellulose material is shown in FIG. 1a. The starting material chitosan is also disclosed in the FIG. 1a.

Chitosan is a linear polysaccharide composed of randomly distributed β-(1-4)-linked D-glucosamine (deacetylated unit) and N-acetyl-D-glucosamine (acetylated unit), chemically derived from the natural compound chitin. In chitin the degree of acetylation is 100%. In chitosan the degree of acetylation can vary from 0.1-99.9%.

Figure 1B:
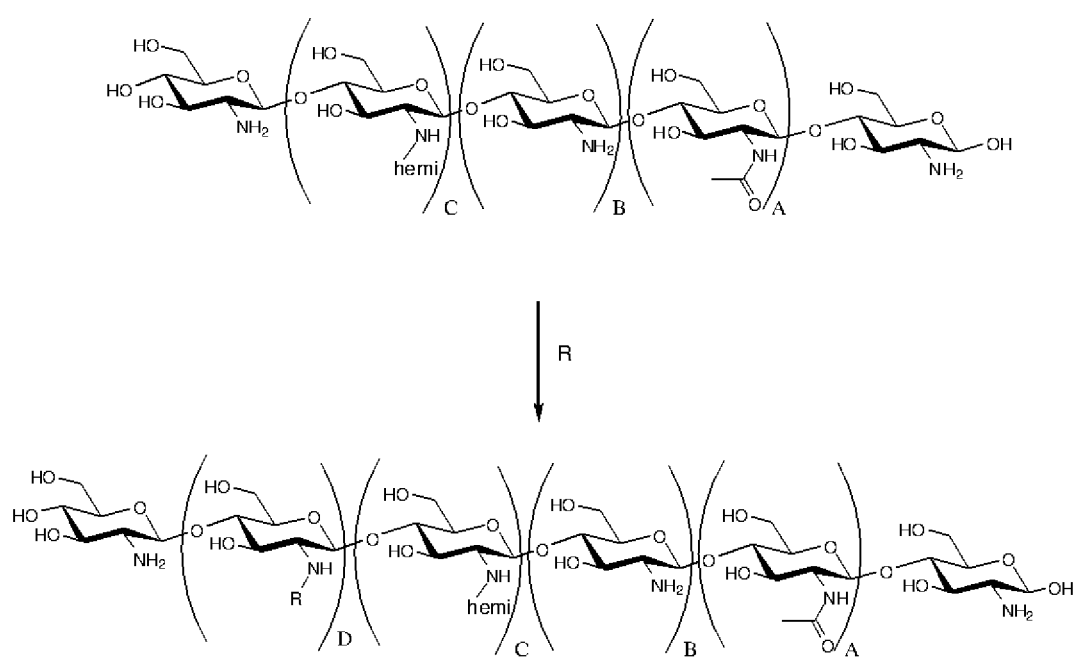
FIG. 1b Show the introduction of R groups to the primary amino groups in the material made of chitosan and a hemicellulose. Hemicellulose modified chitosan is reacting with a R-group resulting in a R functionalised hemicellulose modified chitosan.
Figure 1C:
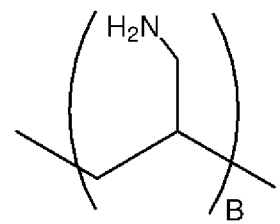
FIG. 1c Show the synthesis of a polymer made of polyallylamine and a hemicellulose FIG. 1d Show the synthesis of a polymer made of polyvinylamine (poly(vinylamine-co-vinylformamide) and a hemicellulose.
Figure 1C:
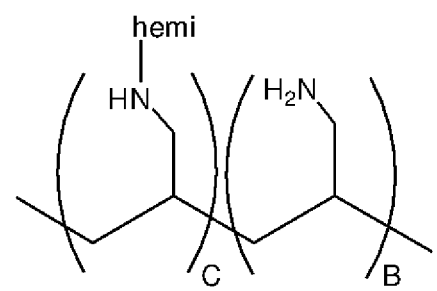
Figure 1D:
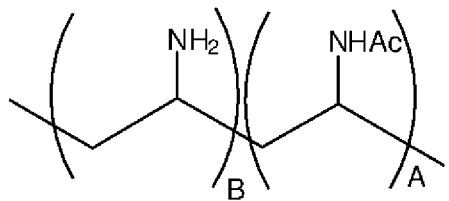
FIG. 1e Show the synthesis of a polymer made of polyethyleneimine and a hemicellulose.
Figure 1D:
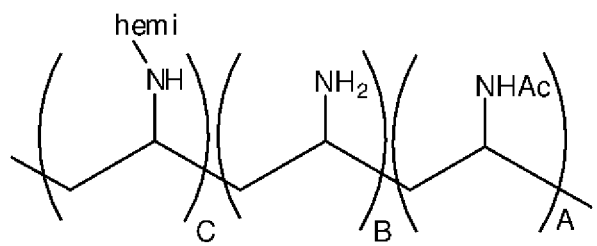
Figure 1E:
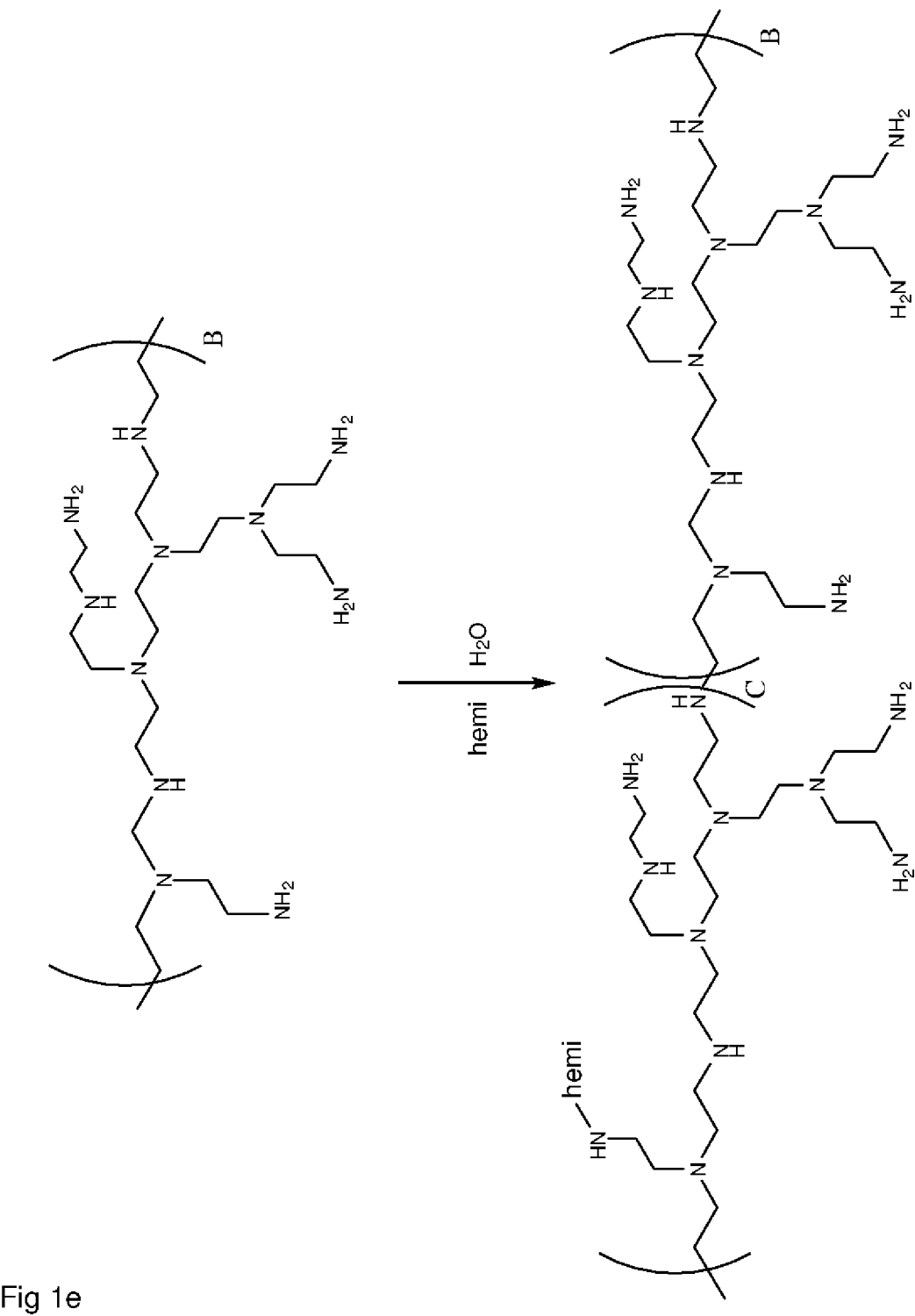

In FIGS. 1a and 1b the references A, B and C relate to amide groups (N-acetyl groups), amine groups and hemicellulose substituted amine groups, respectively. These groups are situated in a random order in the formula. Chitosan with any degree of acetylation can be used in the invention, where the acetylation may vary from 0.1-99.9%, 0.1-50%, 5-40%, 10-30% or 20-26%.

Chitosan with a molecular weight of 50 kDa-190 kDa comprises about 300 to 1200 amino/amide groups. When the degree of N-acetylation is around 25% about 75 to 300 of all amino/amide groups in chitosan corresponds to acetylated units, see FIG. 1a.

Further, the chitosan may have a molecular weight of 179 Da-375 kDa and xyloglucan may have a molecular weight of 1 kDa-2000 kDa or a molecular weight of 1.2 kDa-2000 kDa.

The chitosan may have a molecular weight of 375 kDa or more.

According to the present invention, a polymer may be made of chitosan and xyloglucan. The chitosan is covalently bound to xyloglucan. The chitosan and xyloglucan may be bound to each other by reductive amination between free amino groups of the chitosan and reducing end of xyloglucan. An object with the present invention is to provide a cross-linking agent and/or a cellulose adsorbing agent composition comprising a water soluble material made of chitosan and xyloglucan.

A preferred property for a cross-linking agent is that it can bind very well and fast to cellulose. The adsorbing property can also be used to introduce different properties to the cellulose product. Different functional groups can be introduced to the polymer via the free amino groups or the hydroxyl groups. The cross-linking agent can have several functional groups attached and the density of the functional group can be controlled, this will give the advantage to control the level of the desired property of the cellulose product. This modification of cellulose can be used in e.g., laundry application, making fire retardant cellulose products, or antibacterial and antifungal properties for cellulose product.

An additional object is to provide a cellulose containing product comprising a cross-linking agent and/or a cellulose adsorbing agent composition comprising a water soluble material made of chitosan and xyloglucan. However, the material made of chitosan and xyloglucan may not be water soluble. Further, it is referred to the use of the polymer made of chitosan and xyloglucan as a cross-linking agent.

A polymer made of chitosan and xyloglucan is surprisingly adsorbing well and fast to paper, pulp and textile. The polymer made of primary amine functionalised polymer and hemicellulose adsorbed surprisingly well to pulp and textile material, see FIG. 4a-f and table 3-4. In table 3 and 4 are different polymers according to the present invention disclosed. In table 3 and 4 different xyloglucans are shown for comparison. Further, the percent of the polymer adsorbed on pulp and cotton textile is disclosed in table 3 and 4, respectively.

It has surprisingly been found within the present invention that when xyloglucan is aminated with chitosan it forms a reaction product which, when used as a cross-linking agent in papermaking, confers superior folding endurance strength to the paper product obtained. In addition, further tests as shown in the examples below, have shown good results with polymers made of primary amine functionalized polymer and hemicellulose when applied in paper sheets. Further, when used with textiles, its adsorption to textile is very good.

In the present invention, the xyloglucan may be an oligosaccharide comprising at least 7 monosaccharides (XGO) to polysaccharides comprising at least 15000 monosaccharides (native xyloglucan). The xyloglucan may have a molecular weight of 1 kDa to 2000 kDa.

Any type of chitosan may be used according to the invention. Chitosan with a molecular weight of 179 Da to >375 kDa or (according to Sigma Aldrich) chitosan fragments with lower molecular weights may be used. Chitosan fragments are easy to synthesize and convenient to handle.

The material made of e.g. chitosan and xyloglucan can be made water soluble at neutral pH, which was unexpected. Xyloglucan is water soluble independent of the pH. Chitosan is not soluble above pH ~5.9. By linking xyloglucan covalently to chitosan, the end product can become water soluble at neutral pH. The solubility of the invented material in different pH can be controlled by altering the molecular weight and/or the substitution degree of the water soluble hemicellulose, this is showed in table 1. Different polymers made of chitosan and xyloglucan are shown in the table 1 and 2. They are made according to example 3 below. + is indicating that the compound is water soluble at the given pH, while − is indicating that the compound is not water soluble at the given pH.

TABLE 1

Compound solubility

| Compound | Solubility in pH 4 | Solubility in pH 7 | Solubility in pH 10 |
|---|---|---|---|
| 25% XG15kD-LLCH | + | + | + |
| 5% XGO-LCH | + | − | − |
| 10% XGO-LCH | + | − | − |
| 20% XGO-LCH | + | + | + |
| 50% XGO-LCH | + | + | + |
| 25% XGO-MCH | + | + | + |
| 5% XG4kD-LCH | + | − | − |
| 10% XG4kD-LCH | + | + | − |
| 2% XG15kD-LCH | + | − | − |
| 5% XG15kD-LCH | + | + | − |
| 10% XG15kD-LCH | + | + | + |
| 15% XG15kD-LCH | + | + | + |
| 10% XG15kD-MCH | + | + | − |
| 10% XG15kD-HCH | + | + | − |
| 5% XG100kD-LCH | + | + | − |
| 0.5% XG100kD-MCH | + | − | − |
| 1% XG100kD-MCH | + | − | − |
| 2% XG100kD-MCH | + | − | − |
| 5% XG100kD-MCH | + | + | − |
| 5% XG100kD-HCH | + | + | − |
| 1% XGnative-LCH | + | + | + |
| 1% XGnative-MCH | + | + | + |
| 1% XGnative-HCH | + | + | + |

Nomenclature:
XG = xyloglucan
XGO = xyloglucan oligosaccharides (1 kDa-1.5 KDa)
XGnative = native xyloglucan
LLCH = Low low molecular weight chitosan (5 kDa)
LCH = Low molecular weight chitosan (50 kDa-190 kDa)
MCH = Medium molecular weight chitosan (190 kDa-310 kDa)
HCH = High molecular weight chitosan (310 kDa to >375 kDa)
Example: 10% XG15kD-LCH
10% of the free amino groups of LCH are covalently linked to XG with a molecular weight of 15 kDa.

A method utilizing reductive amination, which can be applied to covalently bind hemicellulose with a primary amine functionalized polymer, has been developed by the inventors. The synthesis is a one pot procedure, where the hemicellulose is dissolved and then reacted with the amino groups of the primary amine functionalized polymer under reducing conditions. The reproducibility is high. The reductive amination of carbohydrates with a reducing end can be performed in one pot, with the imine formation and reduction occurring concurrently. This is known as direct reductive amination, and is carried out with a reducing agent that is relatively stable in water and reactive in acidic conditions, e.g. sodium cyanoborohydride ($NaBH_3CN$).

The polymer may be produced by reductive amination involving the conversion of a carbonyl group to an amine via an intermediate imine. The imine intermediate can also be used as such as a polymer made of primary amine functionalized polymer and hemicellulose.

The polymer made of primary amine functionalized polymer and hemicellulose e.g. chitosan/xyloglucan material may also be produced by reductive amination involving the conversion of a carbonyl group to an amine via an intermediate imine. The reductive amination of carbohydrates with a reducing end can be performed in one pot, with the imine formation and reduction occurring concurrently as disclosed above.

A method for reductive amination of water soluble xyloglucan with chitosan has been developed by the inventors. The synthesis is a one pot procedure, where xyloglucan (XG) or xyloglucan oligosaccharide (XGO) is dissolved and then reacted with the amino groups in chitosan under reducing conditions.

The polymer made of a primary amine functionalized polymer and hemicellulose may be produced in a reaction mixture.

I) where the reaction mixture is made acidic (adjusted to a pH<7) and then may be incubated under reducing conditions.

II) finally the aminated water soluble carbohydrate can be used as such or can be isolated by precipitation or can be purified by filtration with a cut of filter to remove low molecular weight compounds.

An example of the primary amine functionalized polymer is chitosan and an example of hemicellulose is xyloglucan.

The reducing condition of the method may be hydrogen atmosphere and a catalyst such as platinum, platinum derivatives e.g. platinum oxide or a reducing agent that only reduces imines and enamines and do not reduce carbonyl groups e.g. sodium cyanoborohydride, sodium dithionite or amine borane complexes such as pyridine borane, dimethylamine borane or 2-picoline borane, preferably sodium cyanoborohydride.

The pH of the reaction mixture in I) is preferably adjusted to a pH where the primary amine functionalized polymer is soluble. Chitosan is for example soluble at pH below about 5.9. When it relates to chitosan, the reaction mixture is preferably adjusted to a pH below about 5.9, or in some cases it could be adjusted to a pH of 4.5 to 5.9.

The temperature may be between 20° C. and 100° C., preferably 50-60° C., most preferably about 55° C., to speed up the reaction without causing degradation of the hemicellulose, primary amine functionalized polymer or the reducing agent.

The incubation time in I) may be between 5 and 350 hours. The substantial completion of the reaction may be decided by SEC and the products may be further characterised by NMR or IR.

One example of a polymer is as disclosed above, a polymer made of chitosan and xyloglucan. When making this polymer, the amine groups of the chitosan are reacted with xyloglucan. The number of amine groups of chitosan reacted with xyloglucan may vary depending on reaction conditions. A higher degree of substitution gives higher solubility in water. The number of amine groups in chitosan which are reacted with hemicellulose substituents, C in FIG. 1a, may be 0.01-99.9%. 0.01-30%, 0.5-20%, 0.5-15%, 0.5-10%, 1-8% or 2-5%. Similar percentages can be applied to the non-reacted amine groups in chitosan, i.e. B in the formula in FIG. 1 may be 0-99.9%. 10-90%, 20-80%, 30-70%, 40-50%, 50-60%, 50-80%, 60-80%, or 65-75%. It has been found that when approx 4% of the amine groups of chitosan with molecular weight of 150 kDa are reacted with xyloglucan substituents with a molecular weight of 15 kDa, the folding endurance properties of a paper sheet comprising the xyloglucan/chitosan material is 5-6 times better than the reference made without addition of crosslinker modification, see FIG. 2a. Another example where 10% of the amine groups of chitosan with a molecular weight of 250 kDa are reacted with xyloglucan substituents with a molecular weight of 15 kDa, the folding endurance properties of a paper sheet comprising the xyloglucan/chitosan material is 40 times better than the reference made without addition of crosslinker modification see FIG. 3f.

Further, the present invention relates to a polymer wherein at least one functional group R is bounded to at least one amine group and/or hydroxyl group of the polymer. In FIG. 1b one example of the polymer functionalised with R group is shown, where the R group is linked to an amine. The R groups are selected from the group of ionic groups, hydrophobic groups, uncharged hydrophilic groups, potentially reactive groups such as those containing electrophilic atoms, nucleophiles, enzymatically reactive groups, monomers for polymerisation reactions and/or curing, chromophoric or fluorophoric groups, radioactive isotopes, free-radical precursors and stable free radical moieties, nucleic acid sequences, amino acid sequences, proteins or protein-binding agents, receptors, hormones, vitamins, drugs, firming agent, UV absorbers, antisoiling agents, stain release agents, non-redepositioning agent, dye molecules, radioactive groups, perfumes, enzymes, oil repellent agents, water repellent agents, soil release agents, soil repellent agents, dyes including fabric renewing dyes, hueing dyes, dye intermediates, dye fixatives, lubricants, anti sperm agent, fabric softeners, photofading inhibitors, antiwrinkle/ironing agents, shape retention agents, sunscreens, antioxidants, crease resistant agents, antimicrobial agents, skin benefit agents, anti-fungal agents, anti bacterial agents, insect repellents, photobleaches, photoinitiators, sensates, enzyme inhibitors, bleach catalysts, odor neutralizing agents, pheromones fluorescent brighteners, lipophilic fluids and mixtures thereof.

A polymer wherein at least one functional group R is bounded to at least one amine group and/or hydroxyl group could be considered as a modified polymer.

A scheme for adding a functional group can be seen in FIG. 1b.

Further, at least one functional group R may be bounded via a linking group to at least one amine group and/or hydroxyl group.

Further, functional groups, denoted as R, may be coupled to the remaining primary amine groups or the hydroxyl groups of the polymer made from primary amine functionalized polymer and hemicellulose. The coupling can be made prior to or after adsorption of the polymer made from primary amine functionalized polymer and hemicellulose to a cellulose containing product. The functional group can be attached ionically or covalently to the amine groups or to the hydroxyl groups of the polymer made from primary amine functionalized polymer and hemicellulose.

Furthermore when the polymer made of primary amine functionalized polymer and hemicellulose have been adsorbed to the cellulosic fibres the amino groups of the polymer are intrinsically more reactive than the chemical groups already present in cellulosic fibres and can thus be used for coupling a wide range of other chemicals (R groups) to the fibre surface.

When the polymer made of primary amine functionalized polymer and hemicellulose, e.g. chitosan and xyloglucan, with or without additional functional groups, is adsorbed to the cellulose containing fibres, threads or fabrics they obtain improved properties. Such improved properties are for example improved fabric odor, stain removal, soil release, soil repellency, cleaning, whitening, dyeing, tinting, resistance to dye fading, rejuvenate the appearance of faded black fabrics, softening, improved handling, resistance to pilling, resistance to wrinkling, ease of ironing, crease resistance, transfer of materials to human skin, resistance to abrasion, retention of fabric shape, improved fabric tensile strength, protection from microbial build-up, protection from attack by fungi or insects and/or reduced skin irritation. Further, in paper products improved folding endurance, improved tensile index, tensile stiffness, tensile energy absorption, strain at break, modulus of elasticity, wet strength properties, colouring, charges, retention aids of paper additives, and hydrophobicity are obtained.

Functional groups, R, may be linked to the primary amines or the hydroxyl groups of the polymer made of primary amine functionalized polymer and hemicellulose e.g. chitosan and xyloglucan, either directly, for example through an amide or ester bond, or through a linker group. A linker group may be useful when it is desired to join chemical entities which might not otherwise interact, for example due to lack of chemical reactivity, some other form of chemical incompatibility or steric hindrance.

Examples of chemical groups as suitable R-groups may include ionic groups (cationic, e.g. quaternary amino groups, ammonium groups, carbocations, sulfonium groups, or metal cations, etc.; anionic, e.g., alcoxides, thiolates, phosphonates, carbanions, carboxylates, boronates, sulfonates, Bunte salts, etc.; or zwitterionic, e.g., amino acids, ylides, or other combinations of anionic and cationic groups on the same molecule) or their unionised conjugate acids or bases (as appropriate), hydrophobic groups (alkyl hydrocarbons, e.g, fatty acyl or alkyl groups and unsaturated derivatives, or perfluoro alkanes; or aryl hydrocarbons, e.g., aromatic or polycyclic aromatic hydrocarbons or heterocycles), uncharged hydrophilic groups (e.g. polyethers, such as polyethylene glycol), potentially reactive groups such as those containing electrophilic atoms (e.g., carbonyl compounds, carbocations, alkyl halides, acetals, epoxies, etc.), nucleophiles (e.g., nitrogen, sulfur, oxygen, carbanions, etc.), or monomers for polymerisation reactions and/or curing (free radical, e.g., acrylamide, bromobutyrate, vinyl, styrene, acrylates etc.; or otherwise, e.g., nucleophilic or electrophilic reagents), enzymatically reactive groups (e.g. derivatives of cinnamates) chromophoric or fluorophoric groups (pigments, dyes, optical brighteners, e.g., C.I. dyes, fluorescein, sulforhodamine, pyrene), biotin, radioactive isotopes, free-radical precursors and stable free radical moieties (e.g., TEMPO), nucleic acid sequences, amino acid sequences, proteins or protein-binding agents (e.g., affinity ligands, biotin, avidin, streptavidin, carbohydrates, antibodies, or enzyme substrates or their analogues), receptors, hormones, vitamins and drugs.

Radioactive groups may be coupled to the amine and/or hydroxyl group. Radioactivity can be used for tracer applications and fibre morphology studies. Reactions to incorporate alkyl chains can be made with acetic anhydride, alkenyl succinic anhydride or succinic acid anhydride. Alkenyl succinic anhydride, which is a common paper hydrophobizing agent, can be specifically coupled to the fibre surface via the polymer, potentially increasing retention of this group.

Prior to linking the functional group R with the polymer made of primary amine functionalized polymer and hemicellulose the compound comprising functional R group typically contains a moiety selected from the group consisting of amine, alcohol, aldehyde, ketone, carboxylic acid, sulfonic acid, thiol, acyl halide, alkene, nitro compound, diazonium ion, alkyl halide, alkyl toluenesulfonate, boronic acid, alkyl boranes, alkyl boranic acid and mixtures thereof. Typically, the functional group R and the polymer made of a primary amine functionalized polymer and hemicellulose are linked (conjugated) via a linker group including, but are not limited to, amide, azo compound, carbonate, disulfide, ether, ester, hydroperoxide, imine, imide, nitrate, phosphodiester, phosphate, sulfide, sulfone, ketone, urethane, thioester, triazine and/or sulfonamide functional groups.

In one aspect of the invention, the functional group is linked to the polymer made of primary amine functionalized polymer and hemicellulose e.g. chitosan and xyloglucan through a bond which may be subsequently hydrolysed during washing or drying stages of a wash process. In one aspect, such hydrolysis may be catalysed by a hydrolase enzyme including, but not limited to, a lipase, esterase, cutinase, amidase and mixtures thereof.

Examples of suitable perfume groups include acetyl cedrene, 4-acetoxy-3-pentyltetrahydropyran, 4-acetyl-6-t-butyl-l,l-dimetylindane, 5-acetyl-l,1,2,3,3,6-hexamethyl indane, 6-acetyl-l-isopropyl-2,3,3,5-tetramethylindane, alpha-n-amylcinnamic aldehyde, amyl salicylate, aubepine, aubepine nitrile, aurantion, 2-t-butylcyclohexyl acetate, 2-t-butylcyclohexanol, 3-(p-t-butylphenyl) propanal, 4-t-butylcyclohexyl acetate, 4-t-butyl-3,5-dinitro-2,6-dimethyl acetophenone, 4-t-butyicyclohexanol, benzoin siam resinoids, benzyl benzoate, benzyl acetate, benzyl propionate, benzyl salicylate, benzyl isoamyl ether, benzyl alcohol, bergamot oil, bornyl acetate, butyl salicylate, carvacrol, cedar atlas oil, cedryl methyl ether, cedryl acetate, cinnamic alcohol, cinnamyl propionate, cis-3-hexenol, cis-3-hexenyl salicylate, citronella oil, citronellol, citronellonitrile, citronellyl acetate, citronellyloxyacetaldehyde, cloveleaf oil, coumarin, 9-decen-l-ol, n-decanal, n-dodecanal, decanol, decyl acetate, diethyl phthalate, dihydromyrcenol, dihydromyrcenyl formate, dihydromyrcenyl acetate, dihydroterpinyl acetate, dimethylbenzyl carbinyl acetate, dimethyibenzyicarbinol, dimethylheptanol, dimethyloctanol, dimyrcetol, diphenyl oxide, ethyl naphthyl ether, ethyl vanillin, ethylene brassylate, eugenol, florocyclene, geraniol, geranium oil, geranonitrile, geranyl nitrile, geranyl acetate, 1,1,2,4,4,7-hexamethyi-6-acetyl-l,2,3,4-tetrahydronaphthalene, 1,3,4,6,7,8-hexahydro-4,6,6,7,8,8-hexamethylcyclopenta-2-benzopyran, 2-n-heptylcyclopentanone, 3a,4,5,6,7,7a-hexahydro-4,7-methanol (3)H-inden-6-yl-propionate, 3a-4,5,6,7,7a-hexahydro-4,7-methano-1 (3)H-inden-6-ylacetate, 4-(4'-hydroxy-4'-methylpentyl)-3-cyclo hexenecarbaldehyde, alpha-hexylcinnamic aldehyde, heliotropin, Hercolyn D, hexyl aldone, hexyl cinnamic aldehyde, hexyl salicylate, hydroxycitronellal, i-nonyl formate, 3-isocamphylcyclohexanol, 4-isopropylcyclohexanol, 4-isopropylcyclohexyl methanol, indole, ionones, irones, isoarnyl salicylate, isoborneol, isobornyl acetate, isobutyl salicylate, isobutylbenzoate, isobutylphenyl acetate, isoeugenol, isolongifolanone, isomethyl ionones, isononanol, isononyl acetate, isopulegol, lavandin oil, lemongrass oil, linalool, linalyl acetate, LRG 201, 1-menthol, 2-methyl-3-(p-isopropyl phenyl) propanal, 2-methyl-3-(p-t-butyl phenyl) propanal, 3-methyl-2-pentyl-cyclopentanone, 3-methyl-5-phenyl-pentanol, alpha and beta methyl naphthyl ketones, methyl ionones, methyl dihydrojasmonate, methyl naphthyl ether, methyl 4-propyl phenyl ether, Mousse de chene Yugo, Musk ambrette, myrtenol, neroli oil, nonanediol-l,3-diacetate, nonanol, nonanolide-1,4, nopol acetate, 1,2,3,4,5,6,7,8-octahydro-2,3,8,8-tetramethyl-2-acetyl-naphthalene, octanol, Oppoponax resinoid, orange oil, p-t-amyl cyclohexanone, p-t-butylmethylhydrocinnamic aldehyde, 2-phenylethanol, 2-phenylethyl acetate, 2-phenylpropanol, 3-phenylpropanol, para-menthan-7-ol, para-t-butyl phenyl methyl ether, patchouli oil, pelargene, petitgrain oil, phenoxyethyl isobutyrate, phenylacetaidehyde diethyl acetal, phenyl acetaidehyde dimethyl acetal, phenylethyl n-butyl ether, phenylethyl isoarnyl ether, phenyl ethyl phenyl acetate, pimento leaf oil, rose-d-oxide, Sandalone, styrally acetate, 1,1,4,4-tetramethyl-6-acetyl-7ethyl-l,2,3,4-tetrahydronaphthalene, 3,3,5-trimethyl hexyl acetate, 3,5,5-trimethylcyclohexanol, terpineol, terpinyl acetate, tetrahydrogeraniol, tetrahydrolinalool, tetrahydromuguol, tetra hydromyrcenol, thyme oil, trichloromethylphenylcarbinyl acetate, tricyclodecenyl acetate, tricyclodecenyl propionate, 10-undecen-l-al, gamma undecalactone, 10-undecen-1-ol, undecanol, vanillin, vetiverol, vetiveryl acetate, vetyvert oil, acetate and propionate esters of alcohol in the list above, aromatic nitromusk fragrances, indane musk fragrances, isochroman musk fragrances, macrocyclic ketones, macrolactone musk fragrances, tetralin musk fragrances and mixtures thereof.

Examples of suitable enzymes include protease, amylase, beta-glucanase, lipase, hemi-cellulase, cutinase, pectate lyase, pectin lyase, rhamnogalacturonan lyase, endo-l,4-galactanase, xylanase, arabinanase, alpha-L-7-arabinofuranosidase, mannan endo-l,4-mannosidase, beta mannosidase, beta-l,3-l,4-glucanase, rhamnogalacturonan hydrolase, exo-polygalacturonase, rhamnogalacturonase, glucan 1,3-beta-glucosidase, glucan endo-l,6-beta-glucosidase, mannan 5 endo-1,4-beta-mannosidase, endo-1,4-beta-xylanase, cellulose 1,4-cellobiosidase, cellobiohydrolase, polygalacturonases, acetyl and methyl esterase enzymes such as: rhamnogalacturonan methyl esterase, rhamnogalacturonan acetyl esterase, pectin methylesterase, pectin acetylesterase, xylan methyl esterase, acetyl xylan esterase, feruloyl esterase, cinnamoyl esterase and mixtures thereof.

Examples of suitable fluorescent brighteners include C.I. Fluorescent Brighteners 1 through 396, and those belonging to the classes of diaminostilbene sulfonic acid derivatives, diarylpyrazoline derivatives, bisphenyl-distyryl derivatives and mixtures thereof. An example of a primary amine functionalized polymer-hemicellulose with fluorescent brightener group, suitable for improving the whiteness perception of laundered fabrics as part of laundry treatment compositions, or for improving the whiteness perception of paper.

Examples of suitable oil, water or soil repellent agents include silicone derivatives; fluoropolymers; perfluoro $C_1$-$C_{50}$ alkylamines; perfluoro $C_1$-$C_{50}$ carboxylic acids; olefinic/acrylic polymers comprising a combination of alpha, beta unsaturated carboxylated monomers, and olefinic monomers such as styrene, alpha methyl styrene ("AMS") or blocked alpha, beta unsaturated esterified carboxylates or amides; carboxylated polymer salts; low molecular weight carboxylated water soluble polymers (below molecular weight of 10,000) which may or may not contain some sulfonated material such as sulfonated castor oil, or formaldehyde/sulfonated phenol condensate.

Examples of suitable dyes include C.I. Acid Yellow 1 through 262, C.I. Acid Orange 1 through 181, C.I. Acid Red 1 through 449, C.I. Acid Violet 1 through 313, C.I. Acid Blue 1 through 360, C.I. Acid Green 1 through 125, C.I. Acid Brown 1 through 474, C.I. Acid Black 1 through 244, C.I. Basic Yellow 1 through 108, C.I. Basic Orange 1 through 69, C.I. Basic Red 1 through 118, C.I. Basic Violet 1 through 51, C.I. Basic Blue 1 through 161, C.I. Basic Green 1 through 16, C.I. Basic Brown 1 through 23, C.I. Basic Black 1 through 11, C.I. Direct Yellow 1 through 177, C.I. Direct Orange 1 through 122, C.I. Direct Red 1 through 277, C.I. Direct Violet 1 through 110, C.I. Direct Blue 1 through 314, C.I. Direct Green 1 through 105, C.I. Direct Brown 1 through 250, C.I. Direct Black 1 through 204, C.I. Reactive Yellow 1 through 213, C.I. Reactive Orange 1 through 139, C.I. Reactive Red 1 through 283, C.I. Reactive Violet 1 through 47, C.I. Reactive Blue 1 through 274, C.I. Reactive Green 1 through 33, C.I. Reactive Brown 1 through 50, C.I. Reactive Black 1 through 51 and mixtures and analogues thereof.

Examples of suitable dye intermediates include 8-amino-1-naphthol-3,6-disulfonic acid (H-acid), 4,4'-Diamino Benzo Sulphon Aniline (DASA), Gama acid, Broenners acid, Meta Phenylene diamine 4, Sulphonic Acid (MPDSA), 3,3'-dichlorobenzaldazine (DCB).

Examples of suitable lubricants include silicones, waxes and sugar polyesters such as sucrose polyesters, glucose polyesters and cellobiose polyesters.

Examples of suitable fabric softeners include alkyl-modified quaternary ammonium compounds such as diester quaternary ammonium compounds (DEQA); poly quaternary ammonium compounds; triethanolamine esterified with carboxylic acid and quaternized (so called "esterquat"), amino esterquats, cationic diesters, betaine esters, betaines, silicone or silicone emulsions comprising aminosilicones, cationic silicones, quat/silicone mixtures, functionalized polydimethyl siloxane and mixtures thereof.

Examples of suitable photofading inhibitors include UV absorbers. Suitable molecules typically have an extinction co-efficient greater than 2000 $1 \, mol^{-1} \, cm^{-1}$ at a wavelength of maximal absorption. Typically, suitable UV absorbers have a maximal absorption at wavelengths of from about 290 to about 370 nm, from about 310 to about 350 nm, or even from about 330 to about 350 nm. Examples of UV absorbers, listed as sunscreens, are given in Cosmetic Science and Technology Series, Vol. 15; Sunscreens; 2nd edition; edited by Lowe, Shoath and Pathak; Cosmetics and Toiletries; Vol. 102; March 1987.-pages 21-39; and Evolution of Modern Sunscreen Chemicals; pages 3-35 both by N. A. Saarth. Suitable UV absorbers include, but are not limited to, compounds active through non-radiative deactivation; derivatives of benzophenone with substituents in the 2- and/or 4-position; substituted benzotriazoles, for example, water-soluble benzenesulfonic acid-3-(2H-benzotriazol-2-yl)-4-hydroxy-5-(methylpropyl)-monosodium salt); acrylates phenyl-substituted in the 3-position (cinnamic acid derivatives), optionally with cyano groups in the 2-position; salicylates; organic Ni complexes; umbelliferone; endogenous urocanic acid and mixtures thereof.

In one aspect, biphenyl derivatives, stilbene derivatives and mixtures thereof are useful. Suitable UV-B absorbers, include, but are not limited to, camphor derivatives including 3-benzylidenecamphor, 3-(4-methylbenzylidene)camphor, 3-benzylidene-norcamphor and mixtures thereof; 4-aminobenzoic acid derivatives, including 4.(dimethylamino)benzoic acid 2-ethyihexyl ester, 4-(dimethylamino) benzoic acid 2-octyl ester, 4-(dimethylamino)benzoic acid amyl ester and mixtures thereof; esters of cinnamic acid, including 4-methoxycinnamic acid 2-ethylhexyl ester, 4-methoxycinnamic acid propyl ester, 4-methoxycinnamic acid isoamyl ester, 2-cyano-3,3-phenylcinnamic acid 2-ethylhexyl ester nd mixtures thereof; esters of salicylic acid including salicylic acid 2-ethylhexyl ester, salicylic acid 4-isopropylbenzyl ester, salicylic acid homomenthyl ester and mixtures thereof; derivatives of benzophenone, including 2-hydroxy-4-methoxybenzophenone, 2-hydroxy-4-methoxy-4-methylbenzophenone 2,2-dihydroxy-4-methoxy-benzophenone and mixtures there of; esters of benzylmalonic acid, including 4-methoxybenzylmalonic acid di-2-ethylhexyl ester; triazine derivatives including, 2,4,6-trianilino-(p-carbo-2-ethyl-1-hexyloxy)-1,3,5-triazine, octyl triazone, dioctyl butamido triazone and mixtures there of; propane-1,3-diones including 1-(4-tert-butylphenyl)-3-(4-methoxyphenyl)propane-1,3-dione; ketotricyclo-(5.2.1.0) decane derivatives; 2-phenylbenzimidazole-5-sulfonic acid and alkali metal, alkaline earth metal, ammonium, alkylammonium, alkanolammonium and glucammonium salts thereof, sulfonic acid derivatives of benzophenones, for example, 2-hydroxy-4-methoxybenzophenone-5-sulfonic acid and salts thereof sulfonic acid derivatives of 3-benzylidenecamphor, such as for example 4-(2-oxo-3-bornylidenemethyl)benzene-sulfonic acid and 2-methyl-5-(2-oxo-3-bornylidene) sulfonic acid and 2-methyl-5-(2-oxo-3-bornylidene)sulfonic acid and salts thereof. Typical UV-A filters are in particular derivatives of benzoylmethane, such as for example l-(4-tert-butyl-phenyl)-3-(4'-methoxyphenyl) propane-1,3-dione, 4-tert-butyl-4'-methoxydibenzoylmethane (Parsol 1789), 1-phenyl-3-(4'-isopropylphenyl)-propane-1,3-dione and also enamine compounds. The UV-A and UV-B filters can of course also be used as mixtures.

Suitable photofading inhibitors of the anti-oxidant type include benzofurans, coumeric acids or derivatives thereof, for example 2-carboxy benzofuran, and bis(p-amino sulfonates, triazine, DABCO derivatives, tocopherol derivatives, tertiary amines and aromatic substituted alcohols eg butylated hydroxytoluene (BHT), Vitamin C (ascorbic acid) and vitamin E.

Examples of suitable agents for antiwrinkle, crease resistance or ease of ironing include fusible elastomers, polyorganosilicones, aminosilicones with sterically hindered functional groups, water-soluble silicone lubricants, and polymeric nanoparticles.

Examples of suitable bleach catalyst agents include those based on complexes of transition metals and zwitterionic or cationic derivatives of dihydroisoquinolinium salts.

Examples of suitable antimicrobial agents include PCMX (para chrometa xylenol), triclosan (2,4,4'-trichloro-2'-hydroxy diphenyl ether), 3,4,4'-trichloro carbanilide, and DTBBP (2,t-butyl-4-cyclohexylphenol).

Examples of suitable skin benefit agents include (a) silicone oils, gums and modifications thereof such as linear and cyclic polydimethylsiloxanes, amino, alkyl alkylaryl and aryl silicone oils; (b) fats and oils including natural fats and oils such as jojoba, soybean, rice bran, avocado, almond, olive, sesame, persic, castor, coconut, mink oils; cacao fat, beef tallow, lard; hardened oils obtained by hydrogenating the aforementioned oils; and synthetic mono, di and triglycerides such as myristic acid glyceride and 2-ethylhexanoic acid glyceride; (c) waxes such as carnauba, spermaceti, beeswax, lanolin and derivatives thereof; (d) hydrophobic plant extracts; (e) hydrocarbons such as liquid paraffins, petroleum jelly, microcrystalline wax, ceresin, squalene, and mineral oil; (f) esters such as cetyl octanoate, myristyl lactate, cetyl lactate, isopropyl myristate, myristyl myristate, isopropyl palmitate, isopropyl adipate, butyl stearate, decyl oleate, cholesterol isostearate, glycerol monostearate, glycerol distearate, glycerol tristearate, alkyl lactate for example lauryl lactate, alkyl citrate and alkyl tartrate; is (g) essential oils such as fish oils, mentha, jasmine, camphor, white cedar, bitter orange peel, ryu, turpentine, cinnamon, bergamont, citrus unshiu, calamus, pine, lavender, bay, clove, hiba, eucalyptus, lemon, starflower, thyme, peppermint, rose, sage, menthol, cineole, eugenol, citral, citronelle, borneol, linalool, geraniol, evening primrose, camphor, thymol, spirantol, pinene, limonene and terpenoid oils; (h) lipids such as cholesterol, ceramides, sucrose esters and pseudo-ceramides (i) vitamins such as A and E, and vitamin alkyl esters, including those vitamin C alkyl esters; (j) sunscreens such as octyl methoxyl cinnamate and butyl methoxy benzoylmethane (Parsol 1789); (k) Phospholipids; and mixtures of any of the foregoing components.

Examples of suitable antifungal agents include 6-acetoxy-2,4-dimethyl-m-dioxane, diiodomethyl-p-tolysulphone, 4,4-dimethyloxazolidine, hexahydro-l,3,5-tris(2-hydroxyethyl)-s-triazine, sodium dimethyldithiocarbamate, sodium 2-mercaptobenzothioazole, zinc dimethyldithiocarbamate, zinc 2-mercaptobenzothiazole, sodium 2-pyridinethiol-1-oxide, sodium 2-pyridinethiol-1-oxide and N-trichloromethylthio-4-cyclohexene-1,2-dicarboximide.

Examples of suitable insect repellents include N-alkyl neoalkanamides wherein the alkyl is of 1 to 4 carbon atoms and the neoalkanoyl moiety is of 7 to 14 carbon atoms, for example, N-methyl neodecanamide; N,N-diethyl meta toluamide (DEET), 2-hydroxyethyl-n-octyl sulphide (MGK 874); N-octyl bicycloheptene dicarboximide (MGK 264); hexahydrodibenzofuran (MGK 11), Di-n-propyl isocinchomerate (MGK 326); 2-Ethyl-1,3-hexanediol, 2-(n-butyl)-2-ethyl-1,3-propanediol, dimethyl phthalate, dibutyl succinate, piperonyl butoxide, pyrethrum, cornmint, peppermint, american spearmint, scotch spearmint, lemon oil, citronella, cedarwood oil, pine oil, limonene, carvone, eucalyptol, linalool, gum camphor, terpineol and fencholic acid.

Examples of suitable photobleaching agents include catalytic photobleaches selected from the group consisting of xanthene dyes including Eosin Y, Phoxine B, Rose Bengal, C.I. Food Red 14 and mixtures thereof, phthalocyanine derivatives including sulfonated zinc phthalocyanine and sulfonated aluminium phthalocyanine.

Suitable photo-initiators include photo-initiators selected from the group consisting of aromatic 1,4-quinones such as anthraquinones and naphthaquinones; alpha amino ketones, particularly those containing a benzoyl moiety, otherwise called alpha-amino acetophenones; alphahydroxy ketones, particularly alpha-hydroxy acetophenones;

Phosphorus-containing photoinitiators, including monoacyl, bisacyl and trisacyl phosphine oxide and sulphides; dialkoxy acetophenones; alpha-haloacetophenones; trisacyl phosphine oxides; benzoin and benzoin based photoinitiators, and mixtures thereof. In another aspect, suitable photo-initiators include photo-initiators selected from the group consisting of 2-ethyl anthraquinone; Vitamin K3; 2-sulphate-anthraquinone; 2-methyl 1-[4-phenyl]-2-morpholinopropan-1-one; (2-benzyl-2-dimethyl amino-1-(4-morpholinophenyl)-butan-1-one; (1-[4-(2-hydroxyethoxy)-phenyl]-2 hydroxy-2-methyl-1-propan-1-one); 1-hydroxy-cyclohexyl-phenyl-ketone; oligo[2-hydroxy 2-methyl-1-[4(1-methyl)-phenyl] propanone; 2-4-6-(trimethylbenzoyl)diphenyl-phosphine oxide, bis(2,4,6-trimethylbenzoyl)-phenyl-phosphine oxide; (2,4,6 trimethylbenzoyl)phenyl phosphinic acid ethyl ester; and mixtures thereof.

Examples of suitable sensates include include menthol, methyl lactate, methoneglycerine acetal, cyclohexanol, 5-methyl-2-(1-methylethenyl)-1,2 propanediol, 3-[5-methyl-2-(1-methylethyl)cyclohexyl]-oxy-1,2-propanediol, N,2,3-trimethyl-2-isopropyl butanamide, and N-ethyl-p-menthan-3-carboxamide.

Examples of suitable enzyme inhibitors include lipase inhibitors and cellulase inhibitors.

Examples of suitable odor neutralizing agents include cyclodextrin derivatives.

Examples of suitable pheromones include 16-androstene and estrene steroids.

Examples of suitable lipophilic fluids include siloxanes, other silicones, hydrocarbons, glycol ethers, glycerine derivatives such as glycerine ethers, perfluorinated amines, perfluorinated and hydrofluoroether solvents, low-volatility nonfluorinated organic solvents, diol solvents, other environmentally-friendly solvents and mixtures thereof.

Compounds that can act as fabric softeners, water repellents, or lubricants when attached to primary amine functionalized polymer-hemicellulose conjugate include without limitation $C_1$-$C_{50}$ alkylamines, $C_1$-$C_{50}$ fatty acids, $C_1$-$C_{50}$ fatty aldehydes and siloxanes [Wagner et al. (1997) Appl. Organometal. Chem. 11:523-538], see also example 12, 13, 16, 17, 18, 22, and 21. Compounds that can act as soil releaser, stain releaser, water- and oil-repellents, and anti-soiling agents include without limitation perfluoro $C_1$-$C_{50}$ alkylamines, perfluoro $C_1$-$C_{50}$ fatty acids, perfluroro $C_1$-$C_{50}$ fatty aldehydes and alkylanilines. Compounds that can act as UV-absorbers include 4-aminobenzoic acid and aniline derivatives. Compounds that can act as anti-microbials include dimethylhydantoin, quaternary ammonium salts, chlorhexidine, 5-chloro-2-(2,4-dichlorophenoxy)phenol, and glucoprotamine [Bohlander et al. U.S. Pat. No. 6,331,607]. Compounds that can act as fluorescent brighteners include but are not limited to stilbene derivatives, 1,2-ethylene bisbenzoxazole derivatives, 2-styrylbenzoxazole derivatives, coumarin derivatives, 1,3-diphenyl-2-pyrazoline derivatives, and naphthalamide compounds. These compounds can all be attached using triazine chemistry.

The present invention also provides a method of manufacturing a cellulose containing product comprising the steps of:
  providing a furnish comprising pulp of cellulose fibres and water;
  adding a cross-linking agent or a cellulose adsorbing agent according to the present invention, and optionally other papermaking additives;
  dewatering the furnish so as to form a fibrous web;
  drying the fibrous web.

An additional method of manufacturing a cellulose containing product comprises the steps of;
  providing a cellulose containing product;
  treating said cellulose product with a cross-linking agent as or a cellulose adsorbing agent according to the present invention, and optionally other additives.

According to the method, the cellulose product may be a paper, paperboard, filter papers, fine papers, banknote paper, newsprint, liner boards, tissue and other hygiene products, sack, Kraft papers or textile.

The present invention also relates to a composition for treatment of a cellulose material, wherein the composition comprises a polymer made of a primary amine functionalized polymer and a hemicellulose, wherein the primary amine functionalized polymer is covalently bound to the hemicellulose. The polymer has all the features as disclosed above. The inventors have surprisingly found that when cellulose material is treated with the composition comprising the polymer according to the present invention, excellent results have been obtained for paper products and for textile products. This is shown in the examples below.

The composition may further comprise a carrier or filler. Suitable carriers or fillers include, but are not limited to, sodium sulphate, sodium acetate, sodium chloride, water, talc, dolomite, calcite and clays.

The present invention also relates to a composition comprising the polymer according to the present invention, wherein the composition is a detergent composition. It has been shown that textiles treated with the polymer shows good hydrophobic properties. This is a feature which is good regarding detergents. When textiles are cleaned and have a hydrophobic surface, they reject dirt from attaching to the textile. This is good both during the cleaning process and for a textile ready to use.

By detergent is meant a washing or cleaning composition for washing or cleaning any kind of fabrics or textiles. The detergent may be in the form of liquid, gel or paste-form, or solid form. Detergents may also sometimes be called shampoo, for example carpet shampoo.

Compositions for detergents may be solids, fluids, soluble pouches containing solids and/or fluids, insoluble capsules containing solids and/or fluids, uncoated or coated tablets, nonwoven sheets impregnated with solid or fluid ingredients.

When such compositions are solids, they may be granular laundry detergents.

When they are solids, they may be tableted laundry detergents coated in a mixture of adipic acid and a cation exchange resin.

Further, when said compositions are fluids, they may be liquid laundry detergents thickened with a shear-thinning structurant.

When compositions are fluids, they may be liquid fabric rejuvenation compositions.

The composition may comprise any combination of material or have any form previously listed.

In addition, the present invention relates to a method of treating a cellulose material, comprising contacting a cellulose material with the composition comprising the polymer according to the present invention.

In the method, the cellulose material is selected from the group of wood, paper, pulp paperboard, filter papers, fine papers, banknote paper, newsprint, liner boards, tissue and other hygiene products, sack, Kraft papers, textile, cellulosic membrane, and mixtures thereof.

The cellulose material may originate from wood, cellulose, plants, cotton, or any other non-wood based cellulose, linen, hemp, flax, viscose, regenerated cellulose, product of cellulose derivatives, ramie, bacterial cellulose, different organisms, such as bacteria, algae, or any other non-wood based cellulose and mixtures thereof.

Further, the cellulose material may be in the form of wood, cellulose nanofibres such as microfibrillated cellulose or nanowhiskers, fibres, threads or fabrics.

The fabric may be a nonwoven fabric or a woven fabric.

The cellulose material may be paper, pulp or cellulose fabrics.

The present invention also relates to a cellulose containing product treated with the polymer according to the present invention. By treated cellulose containing product is meant a product, which may have been impregnated, dipped, sprayed or treated with the polymer or a composition comprising the polymer, in which the polymer is adsorbed to the cellulose in the product.

Further, the present invention relates to the use of the polymer according to the present invention as an additive in detergents.

In addition the present invention relates to the use of the polymer according to any of claims 1 to 9 as a fire retardant agent, biocide (e.g. antibacterial agent, fungicide, spermicide), hydrophobizing agent, paper additive, retention aid for paper additives, foaming agent, sizing agent, flocculant, odor improving agent, stain removal improving agent, soil release improving agent, soil repellency improving agent, cleaning agent, whitening agent, dyeing agent, tinting agent, resistance to dye fading agent, softening agent, resistance to pilling agent, resistance to wrinkling agent, ease of ironing agent, crease resistance agent, transfer of materials to human skin agent, resistance to abrasion agent, retention of fabric shape agent, fabric tensile strength improving agent, protection from microbial build-up agent, protection from attack by fungi or insects agent, reduced skin irritation agent, folding endurance improving agent, tensile index improving agent, tensile stiffness improving agent, tensile energy absorption improving agent, strain at break improving agent, modulus of elasticity improving agent, wet strength agent, colouring agent, plant growth enhancer, water filtration agent, additive in coatings (e.g. in paint, glue, lacquer, varnish).

It is also referred to the use of the polymer according to the present invention as a foaming agent. A foaming agent, in this context relates to an agent, which forms a foam or lather. The polymer having good foaming properties comprises a at least one functional group R bounded to at least one amine group and/or hydroxyl group, wherein R is selected from saturated and unsaturated fatty ends of e.g. propyl, butyl, pentyl, hexyl, heptyl, octyl, nonyl, decyl etc. or longer alkyl chains such as steryl.

Good dying properties are obtained with a polymer wherein at least one functional group R is bounded to at least one amine group and/or hydroxyl group, wherein R contains positive charge.

A cellulose containing product can be a paper, paperboard, filter papers, fine papers, banknote paper, newsprint, liner boards, tissue and other hygiene products, sack, kraft papers, textile, cardboards, a thread such as a cotton thread, woven or non-woven fabric, wood product, pulp, cellulosic membranes, cotton product, linen product, hemp product, flax product, viscose product, product of regenerated cellulose, ramie product, bacterial cellulose product, cellulose product or any other non-wood based cellulose product.

Furthermore, the cellulose containing product may originate from cellulose from different organisms, such as bacteria, algae, or plants, cotton, linen or wood.

The plant, algae and bacterial produced cellulose can also be mixed into the cellulose containing product in order to improve different properties of the cellulose containing product. The cellulose containing product may comprise cellulose which originates from wood cellulose only or a mixture of wood cellulose and cellulose from other origin. Further, as disclosed above, the cellulose containing product may comprise cellulose only from origin other than wood.

An object of the manufacturing invention of a cellulose containing product is to treat the cellulose containing product with a solution comprising the polymer made of primary amine functionalized polymer and hemicellulose, e.g. chitosan and xyloglucan, and optionally other additives can be added concurrently and/or in a stepwise procedure, e.g. addition of CMC (carboxymethyl cellulose) see also example 11, and FIG. 3a-3h. This can be done by dipping the cellulose containing product into the solution or spray the solution onto the cellulose containing product, resulting in adsorption of the material to the cellulose product to e.g. get improved folding endurance strength, antifungal properties, antibacterial properties, laundry benefits, or enhanced fire retardancy.

The invention further relates to a method, wherein the cellulose material is selected from the group of wood, cotton, linen, hemp, flax, viscose, ramie, or any other non-wood based cellulose and mixtures thereof.

Fibres or threads of the cellulose material can be mixed with synthetic fibres or threads, or wool such as mixtures of cotton and spandex, regenerated cellulose and wool, regenerated cellulose and polyester, and cotton and wool.

The polymer made of primary amine functionalized polymer and hemicellulose e.g. chitosan and xyloglucan can bind to the cellulose in an efficient way. Thereby, the polymer made of primary amine functionalized polymer and hemicellulose e.g. chitosan and xyloglucan can work as a crosslinking agent or a cellulose adsorbing agent in cellulose products. Further, it can bind to cellulose materials, such as fibres, threads or fabrics made of cellulose materials in order to improve the properties of the cellulose material.

The polymer made by primary amine functionalized polymer and hemicellulose, e.g. chitosan and xyloglucan, and a modified polymer wherein at least one functional group R is bounded to at least on amine group and/or hydroxyl group may also be used in a fabric softener, a fabric rejuvenation composition, dryer sheet, and/or laundry additive.

Fabrics, threads or fibres will obtain hydrophobic properties when treated with the polymer, made of a primary amine functionalized polymer and a hemicellulose, which has been reacted with a lipophilic R group, see example 12, 13, 16, 17, 18, 21 and 22. This is an advantage during for example laundry. Any dirt will be prevented to return to the fabric and thus not attach to the fabric. This property is also good after the treatment or cleaning, since soil will not get stuck to the fabric when the fabric is in use. Hence, such fabrics used in for example clothing, will not get soiled so easy.

By cleaning is meant cleaning or washing with for example a detergent as defined above. Treatment means any kind of contact with cellulose material, which can be made during manufacturing of threads, fabrics or clothes.

EXAMPLES

TABLE 2

List of synthesised compounds

| Xyloglucan-Chitosan | Hemicellulose-Chitosan | Xyloglucan-Polyamine | R functionalised Xyloglucan-Chitosan |
|---|---|---|---|
| 25% XG15k-LLCH | 0.5% LBG-LCH | 10% XG15k-PVAm | 10% XG15k-LCH-succinyl |
| 5% XGO-LCH | 10% Xyl-LCH | 10% XG15k-PEI | 10% XG15k-LCH-hexyl |
| 10% XGO-LCH | 1% AraXyl-LCH | 10% XG15k-PAA | 10% XG15k-LCH-PEG5000 |
| 20% XGO-LCH | 5% GlcMan-LCH | | 5% XG15k-LCH-octanoyl |
| 50% XGO-LCH | | | 5% XG15k-LCH-pentanoyl |
| 25% XGO-MCH | | | 5% XG15k-LCH-propanoyl |
| 5% XG4k-LCH | | | 20% XGO-LCH-2-hydroxypropyl trimethyl ammonium chloride |
| 10% XG4k-LCH | | | 20% XGO-LCH-succinyl |
| 2% XG15k-LCH | | | 20% XGO-LCH-octanoyl |
| 5% XG15k-LCH | | | 20% XGO-LCH-acetyl |
| 10% XG15k-LCH | | | 5% XG15k-LCH-hexyl |
| 15% XG15k-LCH | | | |
| 10% XG15k-MCH | | | |
| 10% XG15k-HCH | | | |
| 5% XG100k-LCH | | | |
| 0.5% XG100k-MCH | | | |
| 1% XG100k-MCH | | | |
| 2% XG100k-MCH | | | |
| 5% XG100k-MCH | | | |
| 5% XG100k-HCH | | | |
| 1% XGN-LCH | | | |
| 1% XGN-MCH | | | |
| 1% XGN-HCH | | | |

XG = Xyloglucan
XGO = Xyloglucan oligosaccharides (1.0 kDa-1.5 KDa)
XGN = native xyloglucan
LCH = low molecular weight chitosan (50 kDa-190 kDa)
MCH = Medium molecular weight chitosan (190 kDa-310 kDa)
HCH = High molecular weight chitosan (310 kDa to >375 kDa)
Example: 10% XG15kD-LCH
10% of the free amino groups of LCH are covalently linked to XG with a molecular weight of 15 kDa.
PVAm = polyvinylamine
PIE = ployethyleneimine
PAA = polyallylamine
LBG = galactomannan from locust bean gum
Xyl = xylan
AraXyl = arabinoxylan
PEG = polyethylene glycol
GlcMan = glucomannan

Example 1

Chitosan (Mw 50 kDa-190 kDa) (1 g, 0.0067 mmol) and xyloglucan (Mw ~15,000 Da) (2.6 g, 0.17 mmol) were dissolved in a mixture of 25 mL methanol and 25 mL water with 1% acetic acid. The pH was about 4-5. Additional 50 ml of water was added to get a clear solution, followed by addition of sodium cyanoborohydride (109 mg, 1.73 mmol). The reaction was stirred at 55° C. overnight. The reaction mixture was cooled to room temperature followed by precipitation in 1 L of ethanol (95%). The precipitate was collected and redissolved in water and the ethanol residues were removed by evaporation. The resulting solution was freeze dried to yield a white solid of 3.35 g (93%).

Example 2

Hand sheets (60 g/cm$^2$) were made of unrefined pine pulp adsorbed with 2% of the product from example 1. 2% XG (15000) was used as a comparative example and a sheet without additives was used as a control. The hand sheets were made according too ISO 5269-2. The sheets were tested for tensile index and folding endurance strength, see FIGS. 2a and 2b. The folding endurance was tested according to IS05626, the grammage was tested according to ISO 534, and tensile strength was tested according to ISO 1924-3:2005.

Figure 2A:
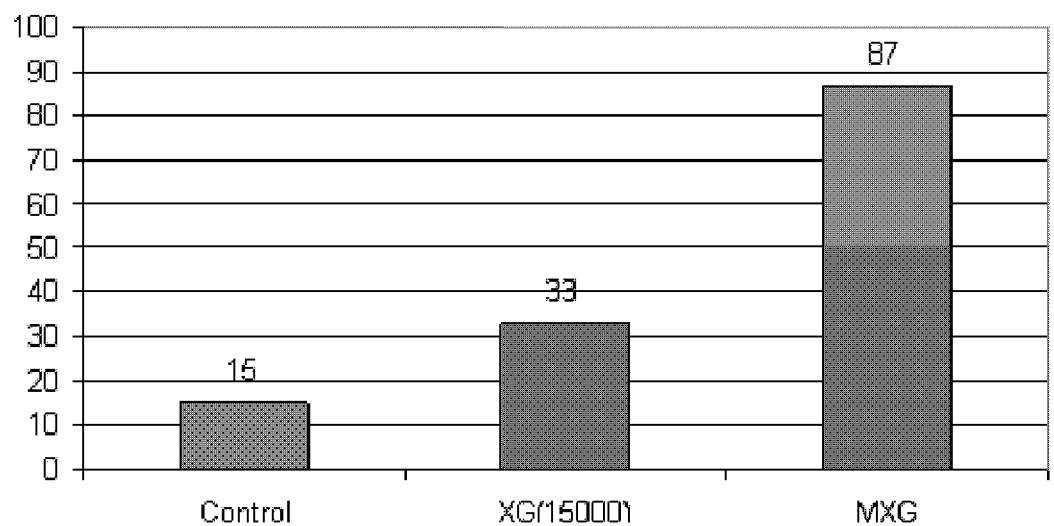
FIG. 2a Shows test results from folding endurance test on paper made from pine pulp. Y-axis: Number of folds FIG. 2b Shows test results from tensile index test on paper made from pine pulp. Y-axis: Nm/g FIG. 3a Shows test results from tensile index test on paper made from pine pulp. Y-axis: Nm/g FIG. 3b Shows test results from tensile stiffness index test on paper made from pine pulp. Y-axis: MNm/kg FIG. 3c Shows test results from tensile energy absorption test on paper made from pine pulp. Y-axis: $J/m^2$ FIG. 3d Shows test results from strain at break test on paper made from pine pulp. Y-axis: %
Figure 2B:
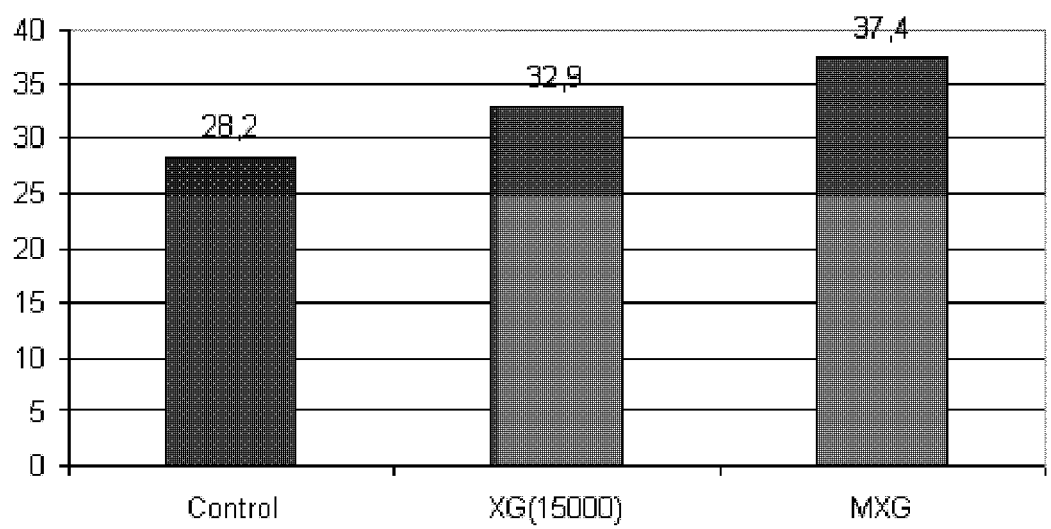
Figure 3A:
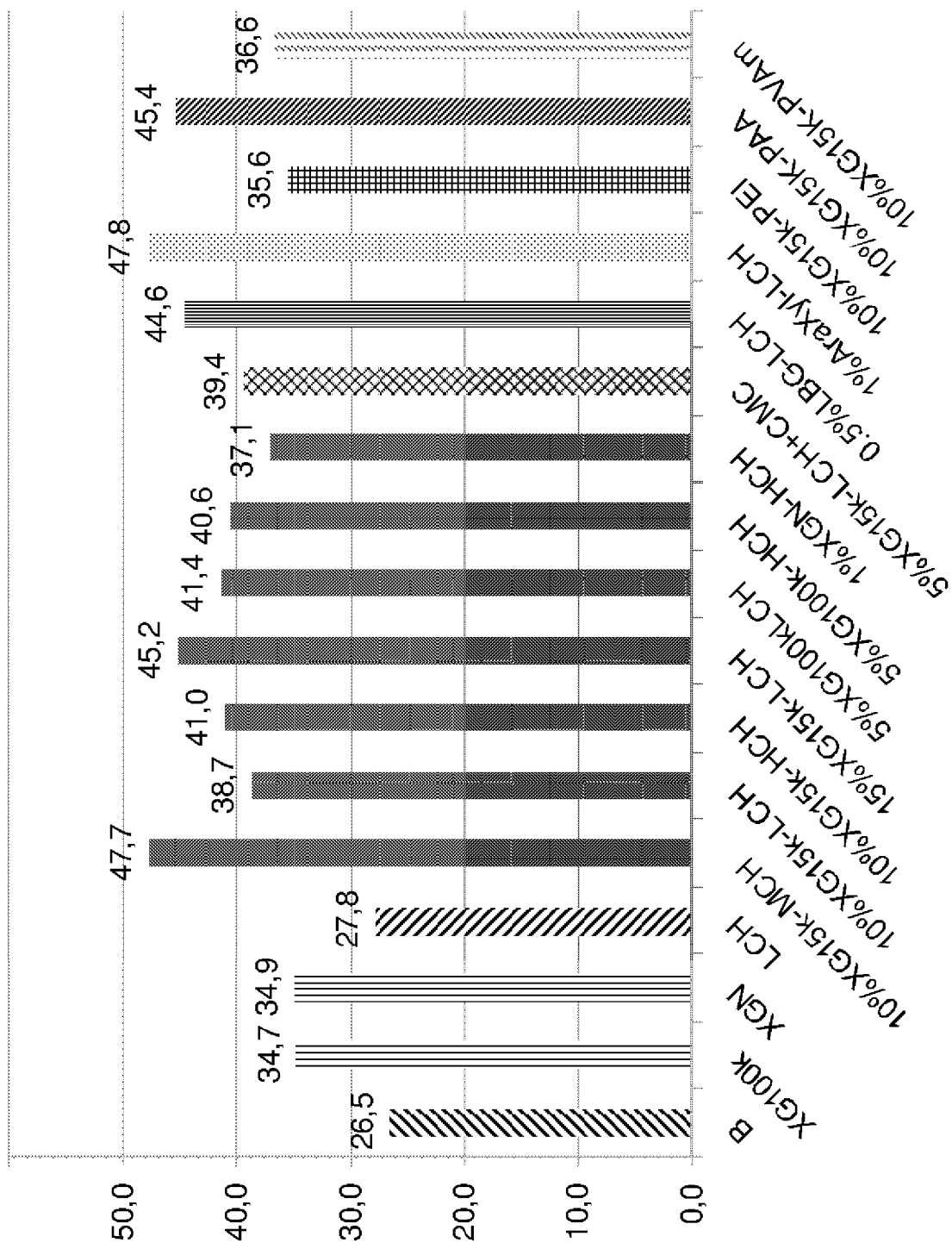
FIG. 3e Shows test results from modulus of elasticity test on paper made from pine pulp. Y-axis: GPa FIG. 3f Shows test results from folding endurance test on paper made from pine pulp. Y-axis: Number of folds FIG. 3g Shows test results from wet strength test on paper made form pine pulp. Y-axis: N/m X-axis: Time (min)
Figure 3B:
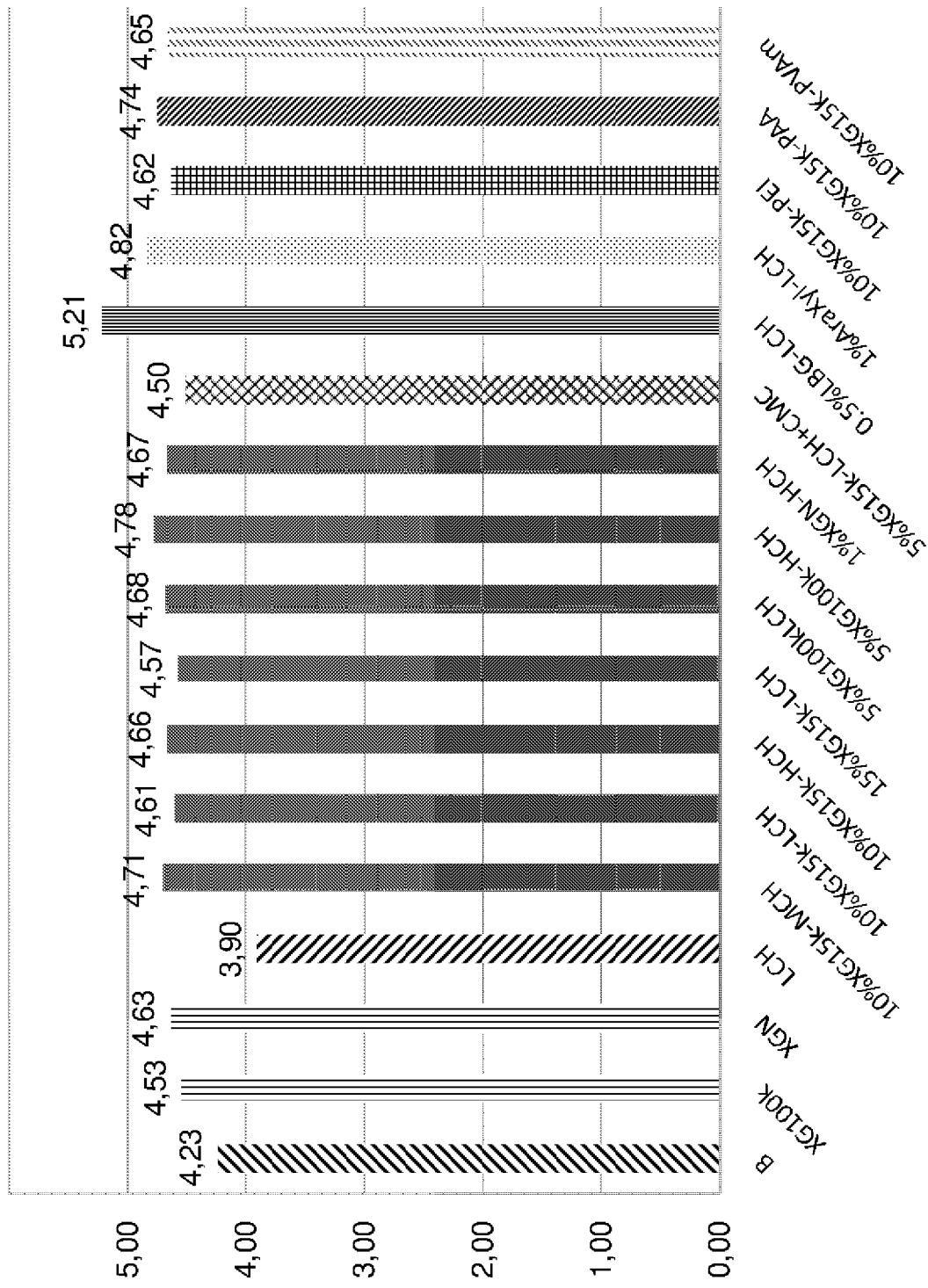
Figure 3C:
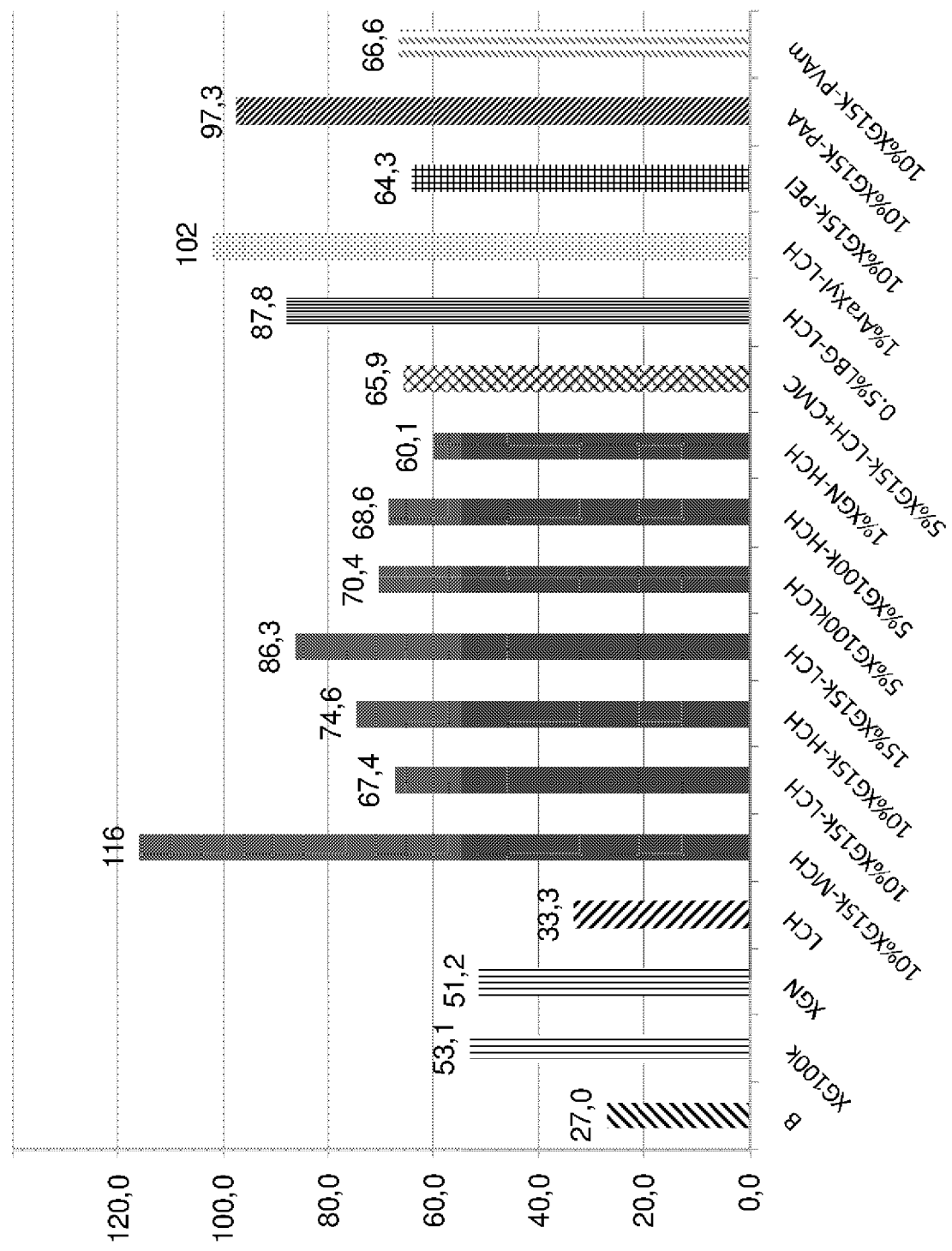
Figure 3D:
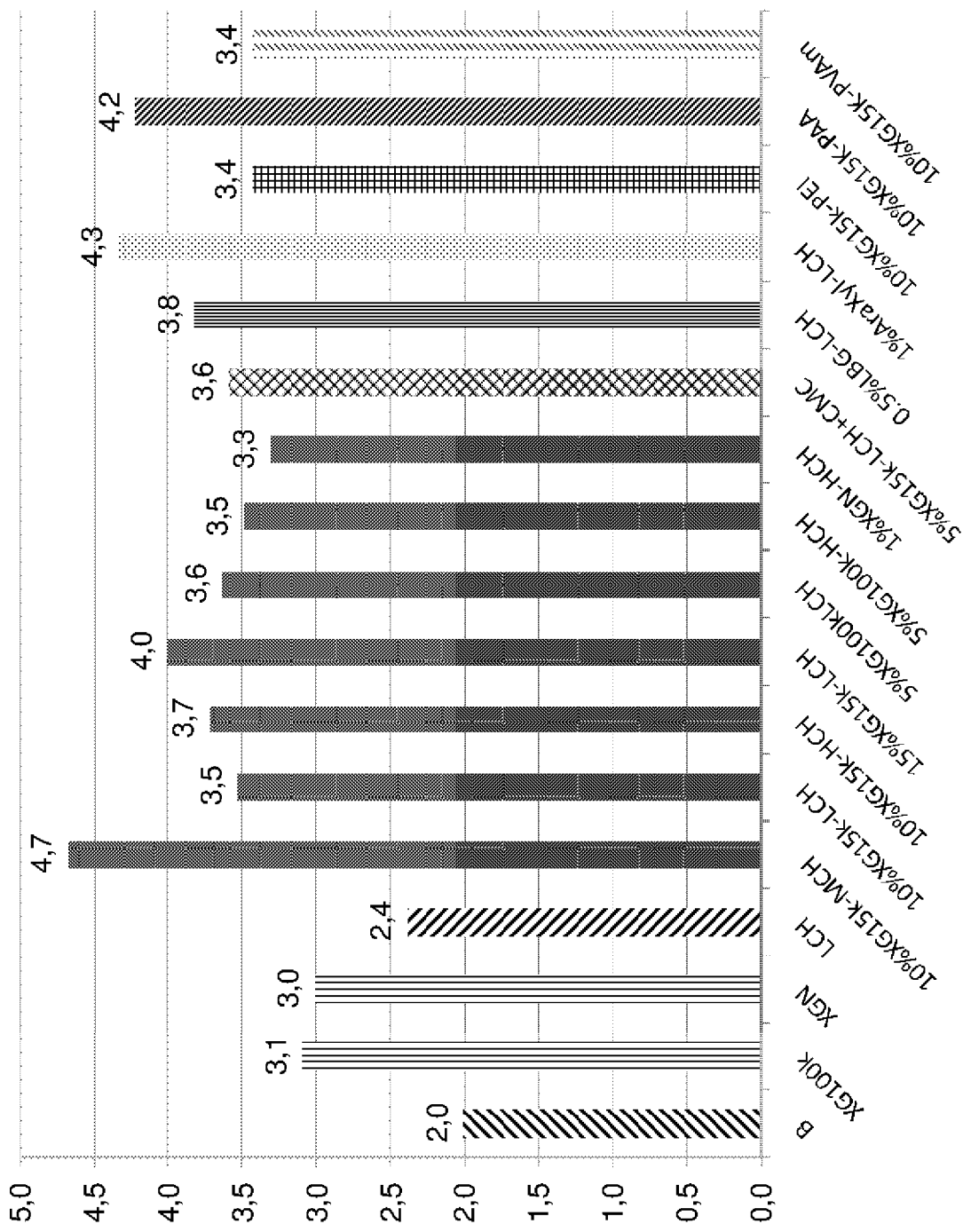
Figure 3E:
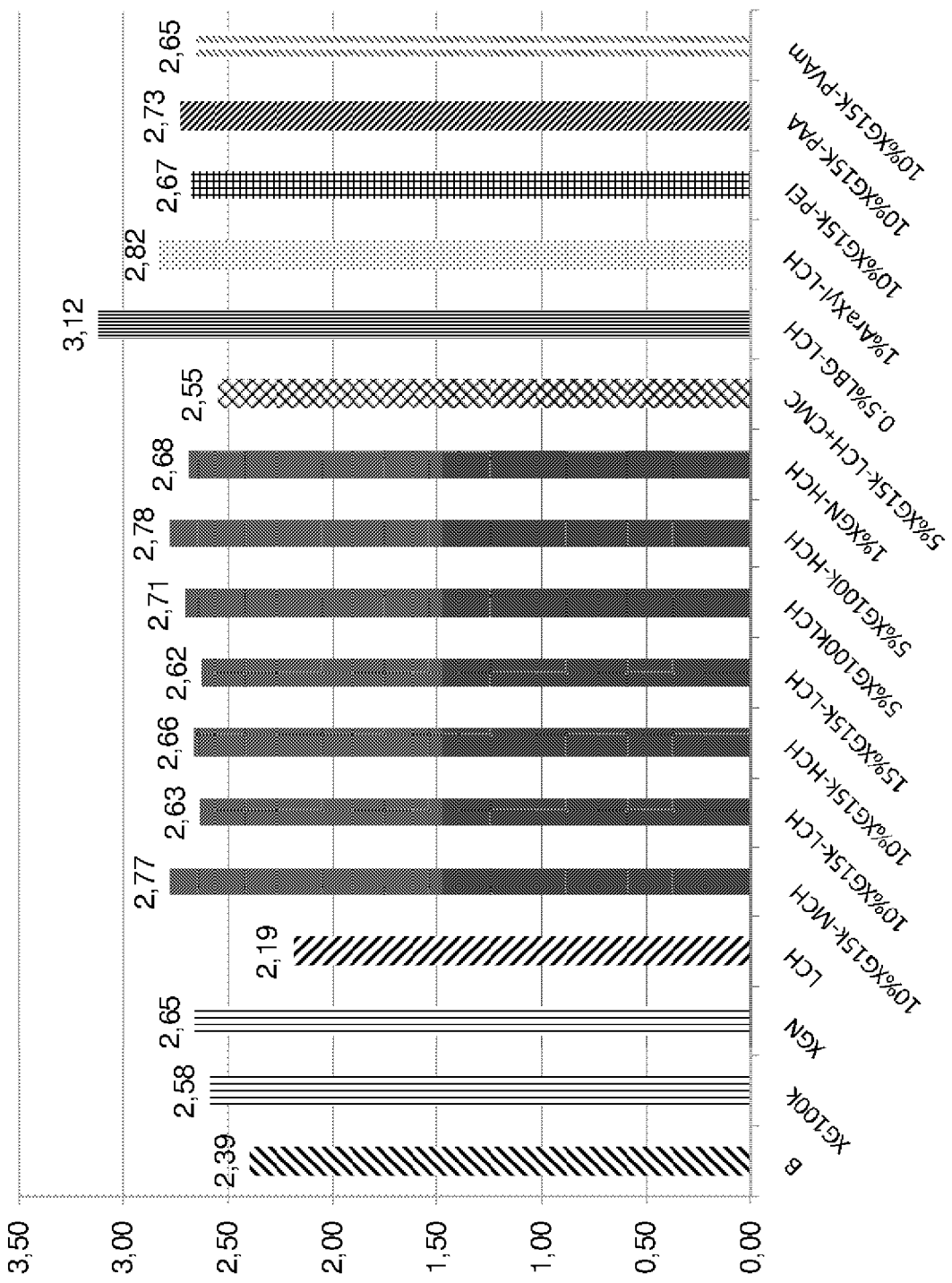
Figure 3F:
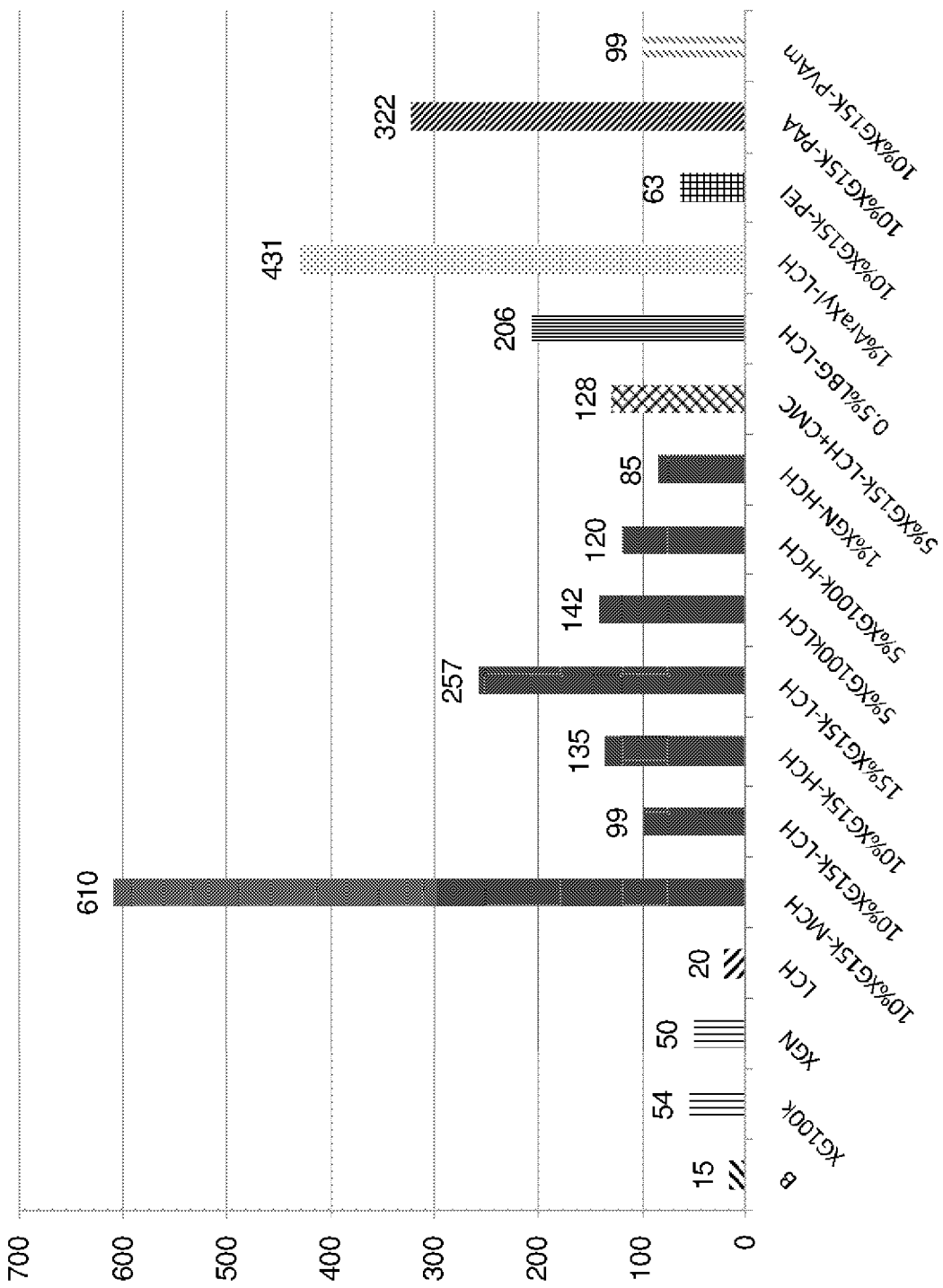
Figure 3G:
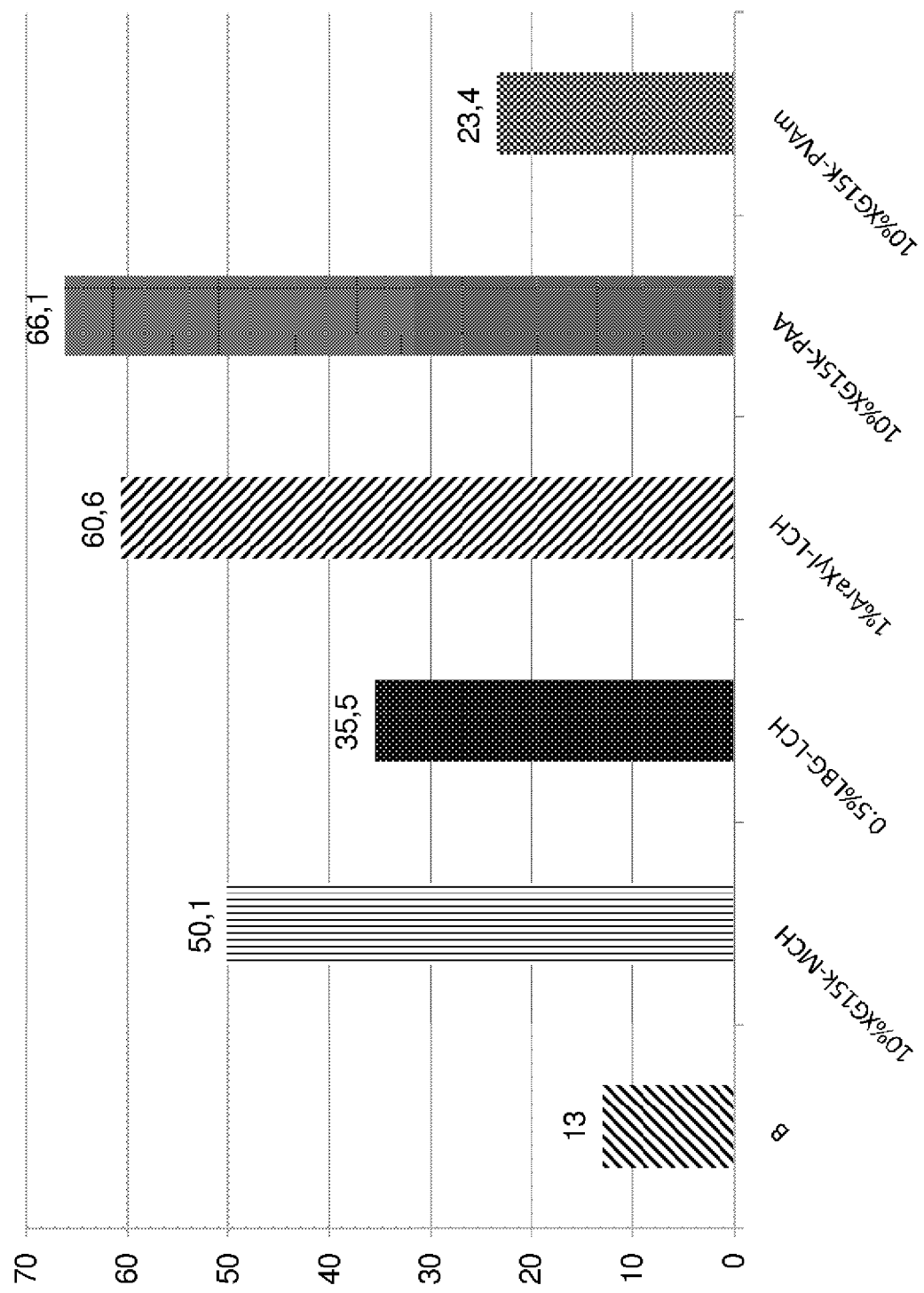

The test results are shown in FIGS. 2a and 2b.

The test results show that the addition of the material made of chitosan and xyloglucan (product prepared according to example 1) results in a paper which has a slightly increased tensile strength and which surprisingly has a folding endurance that is five to six times the folding endurance of the control sheet.

Example 3

A General Procedure for the Synthesis of Polymer Made From xyloglucan-chitosan

Chitosan (Mw 5000 Da, 150 000 Da, 250 000 Da, or 340 000 Da) was dissolved in water with 1-2% acetic acid. The amount of xyloglucan added depends of the desired substitution degree e.g. 1 g of chitosan with MW of 250 000 Da (0,004 mmol) has 1090 free amino groups if the desired substitution degree of xyloglucan with MW 15 000 Da is 5% then ~55 equivalents (3.3 g; 0.22 mmol) of xyloglucan should be added. When the xyloglucan was dissolved the $NaCNBH_3$ was added e.g. for 55 equivalents of xyloglucan (3.3 g; 0.22 mmol) 55 equivalents (14 mg; 0.22 mmol) of $NaCNBH_3$ was added, and the reaction was stirred at 55° C. The reaction was monitored using a DMSO SEC (Size Exclusion Chromatography), monitoring the disappearance of the xyloglucan peak. Every 24 hours the reaction was running new addition of the same amount of $NaCNBH_3$ was added to the reaction. The reaction mixture was cooled to room temperature followed by precipitation in ethanol (95%). The precipitate was collected and redissolved in water and the ethanol residues were removed by evaporation. The resulting solution was freeze dried to yield a white solid. List of synthesised compounds are shown in table 1 and 2.

Example 4

0.5% LBG-LCH (0.5% GalMan-LCH)

The average molecular weight of the galactomannan from locust bean gum was 310 kDa and the molecular weight of chitosan was 50-190 kDa (150 kDa was used in the calculations). The amount of aminogroups in chitosan (150 kDa) were estimated to 870 and the free amino groups (75% deacetylation) were about 650.

Locust bean gum (3.36 g, 0.0108) was dissolved in a 300 mL $H_2O$ containing 3 mL acetic acid at 80° C. The mixture was cooled to 55° C. and chitosan (0.5 g, 0.0033 mmol) and $NaCNBH_3$ (50 mg, 0.79 mmol) were added. The reaction mixture was stirred for 4 days at 55° C. with 4 additions of $NaCNBH_3$ (4×50 mg). The mixture was cooled to room temperature and precipitated in ethanol (4 L). The material was collected by centrifugation and dissolved in $H_2O$. The solution was concentrated before freeze drying to give 3.82 g (99%).

Example 5

10% Xyl-LCH

The average molecular weight of xylan was 16.5 kDa.
Chitosan (1 g, 0.0067 mmol) was dissolved in 200 mL $H_2O$ containing 2 mL AcOH at 55° C. Xylan (7.15 g, 0.43 mmol) and $NaCNBH_3$ (50 mg, 0.79 mmol) were added. The reaction mixture was stirred for 5 days at 55° C. with 4 additions of $NaCNBH_3$ (4×50 mg). The mixture was cooled to room temperature and precipitated in ethanol (4 L).
The material was collected by centrifugation and dissolved in $H_2O$. The solution was concentrated before freeze drying to give 6.5 g (80%).

Example 6

5% GlcMan-LCH

The average molecular weight of glucomannan (GlcMan) was 136 kDa.
Chitosan (0.25 g, 0.00167 mmol) was dissolved in 150 mL $H_2O$ containing 1.5 mL AcOH at 55° C. GlcMan (2.95 g, 0.0217 mmol) and $NaCNBH_3$ (50 mg, 0.79 mmol) were added. The reaction mixture was stirred for 5 days at 55° C. with 4 additions of $NaCNBH_3$ (4×50 mg). The mixture was cooled to room temperature and precipitated in ethanol (4 L). The material was collected by centrifugation and dissolved in $H_2O$. The solution was concentrated before freeze drying to give 3.01 g (94%).

Example 7

1% AraXyl-LCH

The average molecular weight of the arabinoxylan (AraXyl) was 798 kDa.
Chitosan (0.08 g, 0.00053 mmol) was dissolved in 150 mL $H_2O$ containing 1.5 mL AcOH at 55° C. AraXyl (2.766 g, 0.0034 mmol) and $NaCNBH_3$ (50 mg, 0.79 mmol) were added. The reaction mixture was stirred for 5 days at 55° C. with 4 additions of $NaCNBH_3$ (4×50 mg). The mixture was cooled to room temperature and precipitated in ethanol (4 L). The material was collected by centrifugation and dissolved in $H_2O$. The solution was concentrated before freeze drying to give 2.51 g (88%).

Example 8

10% XG15k-PVAm

Polyvinylamine (PVAm) (0.2 g, 0.000588 mmol) was dissolved in 150 mL $H_2O$ containing 1.5 mL AcOH at 55° C. XG15 kDa (6.21 g, 0.441 mmol) and $NaCNBH_3$ (50 mg, 0.79 mmol) were added. The reaction mixture was stirred for 5 days at 55° C. with 4 additions of $NaCNBH_3$ (4×50 mg). The mixture was cooled to room temperature and precipitated in ethanol (4 L). The material was collected by centrifugation and dissolved in $H_2O$. The solution was concentrated before freeze drying to give 5.9 g (92%).

Example 9

10% XG15k-PEI

Polyethyleneimine (PEI) (0.5 g, 0.00067 mmol) was dissolved in 150 mL $H_2O$ containing 1.5 mL AcOH at 55° C. XG15 kDa (5.8 g, 0.39 mmol) and $NaCNBH_3$ (50 mg, 0.79 mmol) were added. The reaction mixture was stirred for 5 days at 55° C. with 4 additions of $NaCNBH_3$ (4×50 mg). The mixture was cooled to room temperature and precipitated in ethanol (4 L). The material was collected by centrifugation and dissolved in $H_2O$. The solution was concentrated before freeze drying to give 6.3 g (100%).

Example 10

10% XG15k-PAA

Polyallylamine (PAA) (0.2 g, 0.0031 mmol) was dissolved in 100 mL $H_2O$ containing 1 mL AcOH at 55° C. XG15 kDa (5.26 g, 0.35 mmol) and $NaCNBH_3$ (50 mg, 0.79 mmol) were added. The reaction mixture was stirred for 5 days at 55° C. with 4 additions of NaCNBH$_3$ (4×50 mg). The mixture was cooled to room temperature and precipitated in ethanol (4 L). The material was collected by centrifugation and dissolved in H$_2$O. The solution was concentrated before freeze drying to give 5.2 g (95%).

Example 11

Hand sheets (60 g/cm$^2$) were made of unrefined pine pulp adsorbed with 2% of the product from example 3-10. In one case CMC was added in the wet end after adsorption of 5% XG15k-LCH. The hand sheets were made according too ISO 5269-2. The sheets were tested for tensile index, tensile stiffness index, tensile energy absorption, strain at break, modulus of elasticity, folding endurance strength and wet strength, see FIGS. 3a to 3h. The folding endurance was tested according to ISO 5626, the grammage was tested according to ISO 534, and tensile strength was tested according to ISO 1924-3:2005.

B refers to a blank test, i.e. a paper sheet without any polymer or material added to the paper sheet and is used for comparison. XG100k, XGN and LCH are also used as comparison tests. All the tested polymers show improved properties compared to the blank and XG100k, XGN and LCH. However, in some specific test, some of the polymers have a result below a result from a comparison test. But in total, the polymers show improved properties tested according to this Example, which can be seen in FIGS. 3a to 3h.

In the following examples (example 12-22) the polymer made of the primary amine functionalized polymer and hemicellulose is further functionalized with R groups on the free primary amines for schematic structure, see FIG. 1b.

Example 12

5% XG15k-LCH-hexyl

5% XG15k-LCH (0.1 g 0.000185 mmol) was dissolved in 10 mL H2O. Hexanal (44 μL, 0.36 mmol) and NaCNBH3 (24 mg, 0.382 mmol) was added and acetic acid was added to obtain a pH of 5. The mixture was stirred at 55° C. for 48 hours. Solids in the mixture were removed by centrifugation and filtration and the product was then precipitated in ethanol. The precipitate was collected by centrifugation and dissolved in water. Concentration and freeze drying gave 100 mg (yield: >98%) of the product. The product from this example showed foaming property.

Example 13

10% XG15k-LCH-hexyl

10% XG15k-LCH (2 g 0.002 mmol) was dissolved in 70 mL H$_2$O. Hexanal (479 μL, 3.99 mmol) and NaCNBH3 (252 mg, 4.0 mmol) was added and acetic acid was added to obtain a pH of 5. The mixture was stirred at 55° C. for 36 hours. The product was precipitated in ethanol and the material was collected by centrifugation (4000 rpm). The precipitate was dissolved in water (the solids that did not dissolve were removed by centrifugation). The solution was concentrated and freeze dried to give 0.850 mg of the product (yield: 43%). The product from this example showed foaming property.

Example 14

10% XG15k-LCH-succinyl

10% XG15k-LCH (2 g, 0.002 mmol) was dissolved in 70 mL H$_2$O. Succinic anhydride (1.3 g, 13 mmol) was added at 0° C. and the reaction was stirred at 0° C. over the night. The solution was poured into ethanol, but no precipitate was formed. NaOH (1 M) was added (to hydrolyse the hydroxyl esters) until pH became 12 and the product started to precipitate. Stirring was continued at a pH of 12 for 1 hour and then the material was collected by centrifugation. The product was dissolved in water and concentrated and freeze dried. Unfortunately the yield was too high indicating impurities (probably succinic acid and sodium salts) so the product was dialysed (SpectraPor Cellulose Ester MWCO 10.000, from Fischer GTF) under continuous deionised water flow for two days. The solution containing the product was concentrated and freeze dried to give 1.065 g (yield: 53%) of the product.

Example 15

10% XG15k-LCH-PEG5000

10% XG15k-LCH (2 g 0.002 mmol) was dissolved in 100 mL H$_2$O at 55° C. Mono methoxy-PEG5000-aldehyde (3.75 g, 0.75 mmol) and NaCNBH$_3$ (250 mg, 3.97 mmol) was added. Acetic acid was added to obtain a pH of 5 and immediately a hard gel was formed. More water (200 mL) was added and the hard gel became less viscous. The mixture was stirred at 55° C. over night. The product was poured into ethanol and the solids were collected by centrifugation. The pellet was not dissolvable in water but the ethanol was evaporated anyway and the residue was freeze dried to give 4.42 g of the product.

Example 16

5% XG15k-LCH-octanoyl

5% XG15k-LCH (0.1 g 0.000185 mmol) was dissolved in a mixture 6 mL H$_2$O-DMF (1:1). Octanoic acid (10 μL, 0.0631 mmol) and triethylamine (17 μL, 0.122 mmol) was added. Finally EDCI (23 mg, 0.120 mmol) was added and the mixture was stirred at rt over night. Solids in the mixture were removed by centrifugation and the clear solution was collected. The pellet and foam was washed with water and the mixture was centrifuged once again and the clear solution was collected. The combined solutions containing the product (as indicated by TLC) was precipitated in ethanol (200 mL) followed by centrifugation to obtain a white material. The material was dissolved in water and the ethanol was removed by concentration. 80 mg (yield: 80%) of the product was obtained after freeze drying. The product from this example showed foaming property.

Example 17

5% XG15k-LCH-propanoyl

5% XG15k-LCH (0.1 g 0.000185 mmol) was dissolved in a mixture 6 mL H$_2$O-DMF (1:1). Propionic acid (10 μL, 0.134 mmol) and triethylamine (34 μL, 0.244 mmol) was added. Finally EDCI (48 mg, 0.250 mmol) was added and the mixture was stirred at rt over night. The clear reaction mixture was precipitated in ethanol (200 mL) and the material was collected by centrifugation. The white material was dissolved in water and the remaining ethanol was removed by concentration. Still some solids remained in the solution and these impurities were removed by centrifugation. The solution containing the product was precipitated once again in ethanol (200 mL) and the white material was collected by centrifugation, dissolved in water and concentrated. The solution was freeze dried to give 52 mg (yield: 52%) of the product. The product from this example showed foaming property.

Example 18

5% XG15k-LCH-pentanoyl

5% XG15k-LCH (0.1 g 0.000185 mmol) was dissolved in a mixture 6 mL H$_2$O-DMF (1:1). Pentanoic acid (10 µL, 0.134 mmol) and triethylamine (34 µL, 0.244 mmol) was added. Finally EDCI (48 mg, 0.250 mmol) was added and the mixture was stirred at rt over night. The clear reaction mixture was precipitated in ethanol (200 mL) and the material was collected by centrifugation. The white material was dissolved in water and the remaining ethanol was removed by concentration. Still some solids remained in the solution and these impurities were removed by centrifugation. The pellet (impurities and product according to TLC) was washed with water and the mixture was centrifuged. The combined clear solutions were pooled and concentrated before freeze drying to give 70 mg (yield: 70%) of the product. The product from this example showed foaming property.

Example 19

20% XGO-LCH-2-hydroxypropyl trimethyl ammonium chloride

The amount of free amino groups in 20% XGO-LCH was estimated to be 520. The aim was to react all free amino groups with glycidyltrimethylammonium chloride.

20% XGO-LCH (1 g, 0.00316 mmol) was dissolved in 30 mL H$_2$O. Glycidyltrimethyl ammonium chloride (0.88 mL, 6.56 mmol) was added and the reaction was stirred at 60° C. over night. The mixture was cooled to room temperature and the product was precipitated in ethanol (0.5 L) and the material was collected by centrifugation. The material was dissolved in water and freeze dried to give 1.05 g of the product.

Example 20

20% XGO-LCH-succinyl

The amount of free aminogroups in 20% XGO-LCH was estimated to be 520. The aim was to react all free amino groups with succinic anhydride.

20% XGO-LCH (1 g, 0.00316 mmol) was dissolved in 30 mL H$_2$O. The solution was cooled to 0° C. and succinic anhydride (0.82 g, 8.2 mmol) was added and the reaction mixture was stirred over night while the temperature was allowed to slowly reach room temperature. The mixture was made basic (pH=12) by the addition of NaOH (10 mL, 1 M) and the mixture was stirred for 1 h at room temperature to hydrolyse unwanted esters. The mixture was neutralised with HCl (1 M) to pH 7 before precipitation in ethanol (0.5 L). The product was collected by centrifugation and dissolved in water, concentrated and freeze dried to give 1.2 g (100%) of the product.

Example 21

20% XGO-LCH-acetyl

20% XGO-LCH (1 g, 0.00316 mmol) was dissolved in 80 mL DMF-H$_2$O 1:1. Acetic acid (0.141 mL, 2.46 mmol), HOBT (0.05 g, 0.37 mmol) and EDCI (0.378 g, 1.97 mmol) were added. The reaction mixture was stirred at room temperature for 4 days. The product was precipitated in ethanol and collected by centrifugation. The material was dissolved in water, concentrated and freeze dried to give 1.01 g of the product.

Example 22

20% XGO-LCH-octanoyl

20% XGO-LCH (1 g, 0.00316 mmol) was dissolved in 80 mL DMF-H$_2$O 1:1. octanoic acid (0.39 mL, 2.46 mmol), HOBT (0.05 g, 0.37 mmol) and EDCI (0.378 g, 1.97 mmol) were added. The reaction mixture was stirred at room temperature for 4 days. The product was precipitated in ethanol and collected by centrifugation. The material was dissolved in water, concentrated and freeze dried to give 1.01 g of the product. The product from this example showed foaming property.

Example 23

A general procedure for adsorption of polymer onto unrefined pine pulp. Adsorption isotherms were made for compound 10% XG15k-MCH (FIG. 4a), 20% XGO-LCH (FIG. 4b), and 10% XG15k-PEI (FIG. 4c), and adsorption after 30 minutes was measured for compounds in table 3. The dry weight of the unrefined pulp was 96%. 30 g pulp (dry weight) was soaked in water for 4 hours before disintegration at 30,000 revolutions with a pulp consistency of 15 g/L. The pulp slurry was diluted to 10 g/l before the addition of the specific compound at a loading ratio of 2% (w/w). The adsorption was performed at room temperature while stirring with mechanical over head stirrer. The reaction time for adsorption isotherm was started when the specific compound was added and samples were taken out from the solution at different time intervals. The samples were analyzed with a colorimetric assay triiodide, see example 25 or brilliant red see example 26. The results can be seen in FIG. 4a-c and table 3, wherein it can be seen that the modified polymers adsorb very well to the pulp.

TABLE 3

| Xyloglucan-Chitosan | Percent adsorbed to Pine pulp after 30 min | Hemicellulose-Chitosan | Percent adsorbed to Pine pulp after 30 min | Xyloglucan-Polyamine | Percent adsorbed to Pine pulp after 30 min | Xyloglucan (for comparison) | Percent adsorbed to Pine pulp after 30 min |
|---|---|---|---|---|---|---|---|
| 5% XG15k-LCH | 89% | 0.5% LBG-LCH | 73% | 10% XG15000-PVAm | 66% | XG15k | 92% |
| 15% XG15k-LCH | 82% | 1% AraXyl-LCH | >99% | 10% XG15000-PEI | 59% | XG100k | 35% |
| 10% XG15k-MCH | 93% | | | 10% XG15000-PAA | 93% | XGN | 36% |
| 10% XG15k-HCH | 90% | | | | | | |
| 5% XG100k-LCH | 52% | | | | | | |
| 5% XG100k-HCH | 75% | | | | | | |
| 1% XGN-HCH | 34% | | | | | | |

Example 24

Figure 4A:
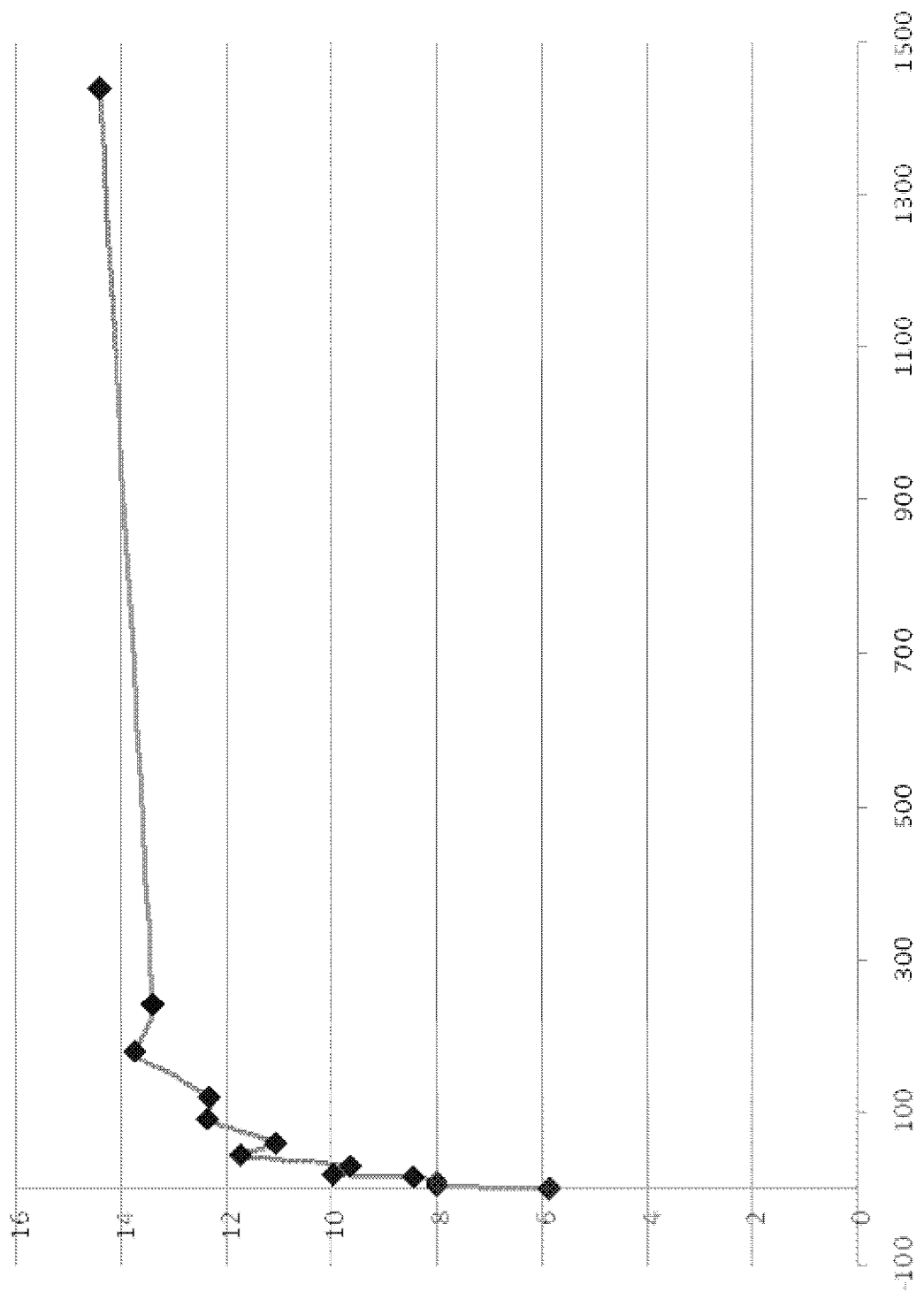
FIG. 4a Adsorption isotherm of 10% XG15k-MCH on unrefined pine pulp. Y-axis: Adsorption (mg adsorbed 10% XG15k-MCH/g pulp) X-axis: Time (min)
Figure 4B:
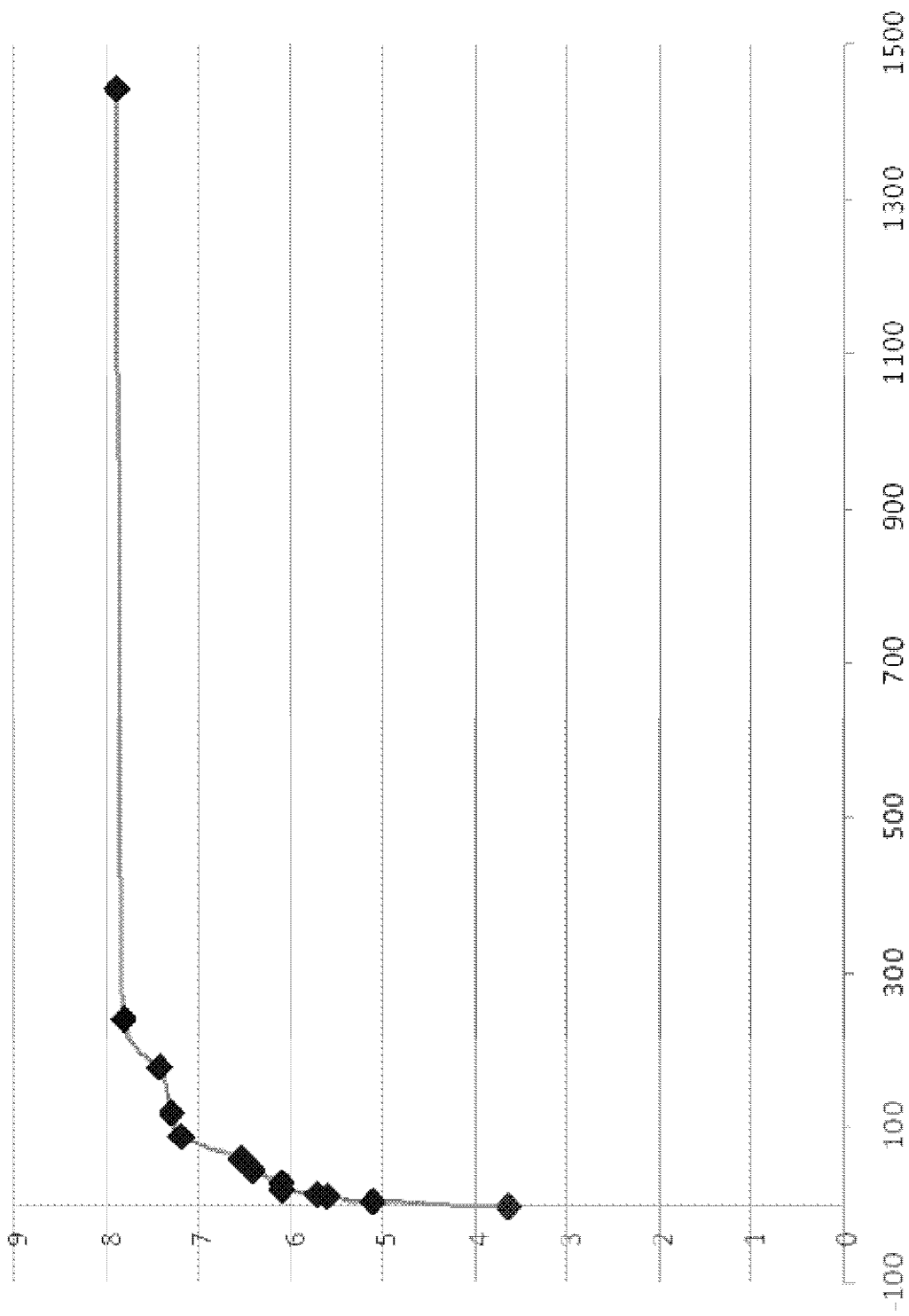
FIG. 4b Adsorption isotherm of 20% XGO-LCH on unrefined pine pulp. Y-axis: Adsorption (mg adsorbed 20% XGO-LCH/g pulp) X-axis: Time (min)
Figure 4C:
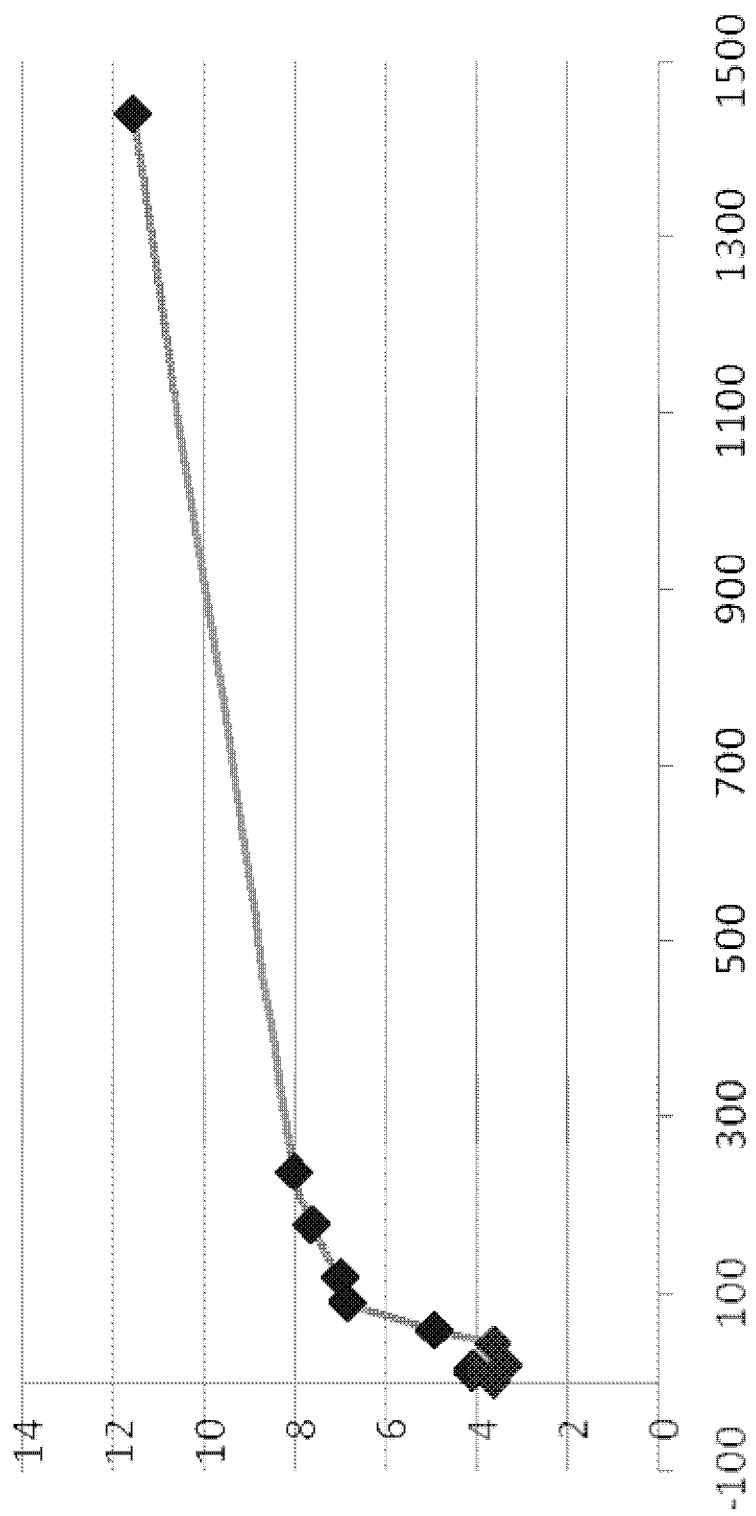
FIG. 4c Adsorption isotherm of 10% XG15k-PEI on unrefined pine pulp. Y-axis: Adsorption (mg adsorbed 10% XG15k-PEI/g pulp) X-axis: Time (min)
Figure 4D:
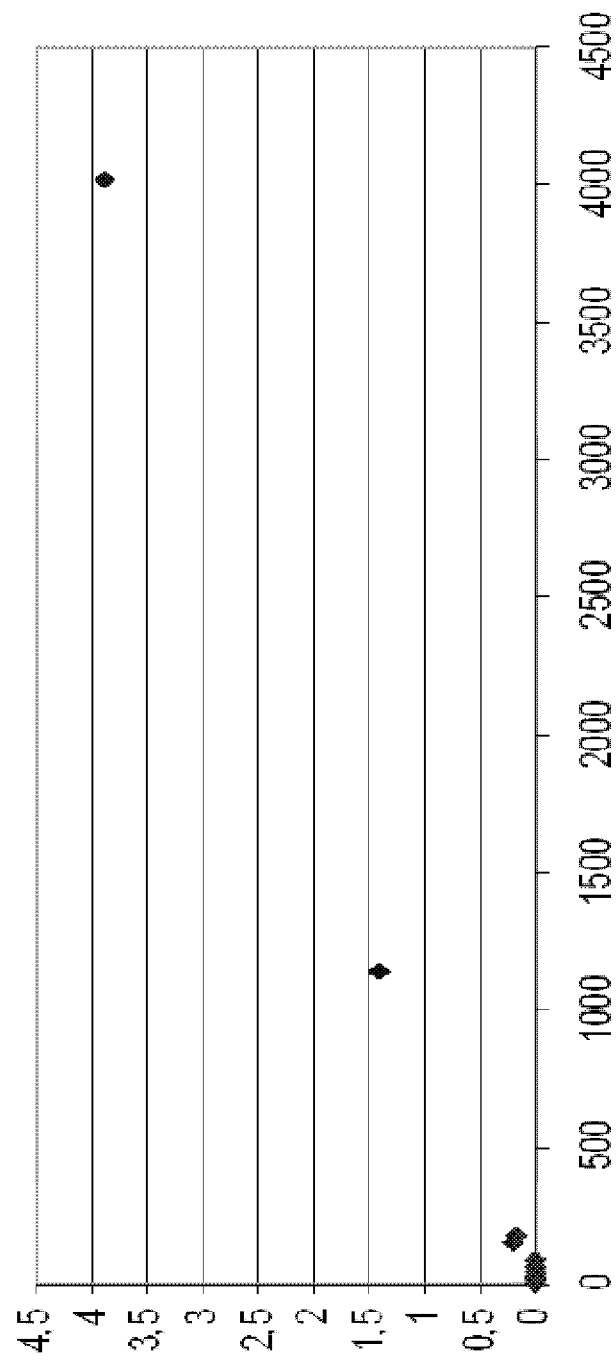
FIG. 4d Adsorption isotherm of XG100 kDa on cotton fabric for comparison. Y-axis: Adsorption (mg adsorbed XG100 kDa/g cotton) X-axis: Time (min)
Figure 4E:
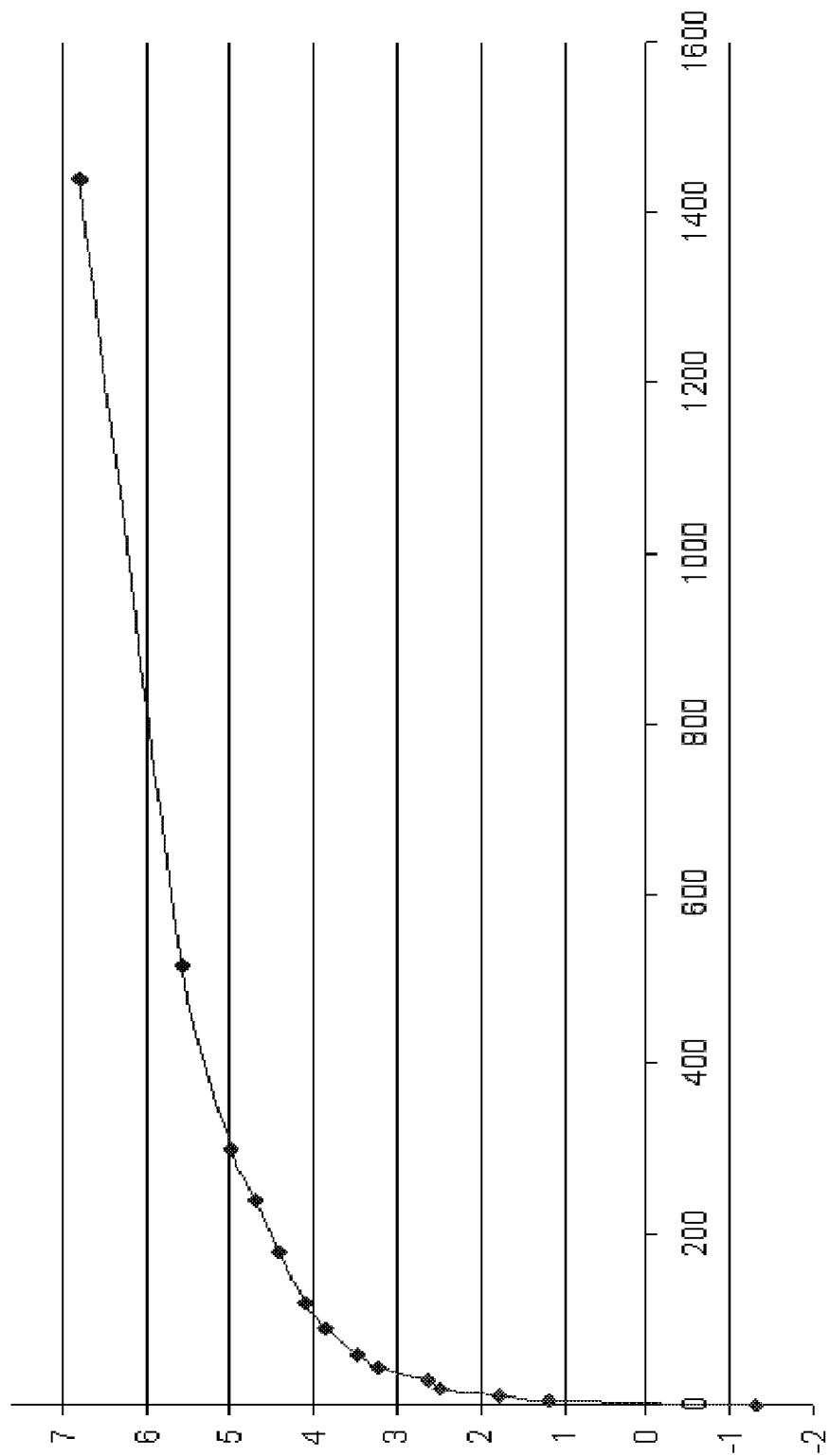
FIG. 4e Adsorption isotherm of 20% XGO-LCH to cotton fabric. Y-axis: Adsorption (mg adsorbed 20% XGO-LCH/g cotton) X-axis: Time (min)
Figure 4F:
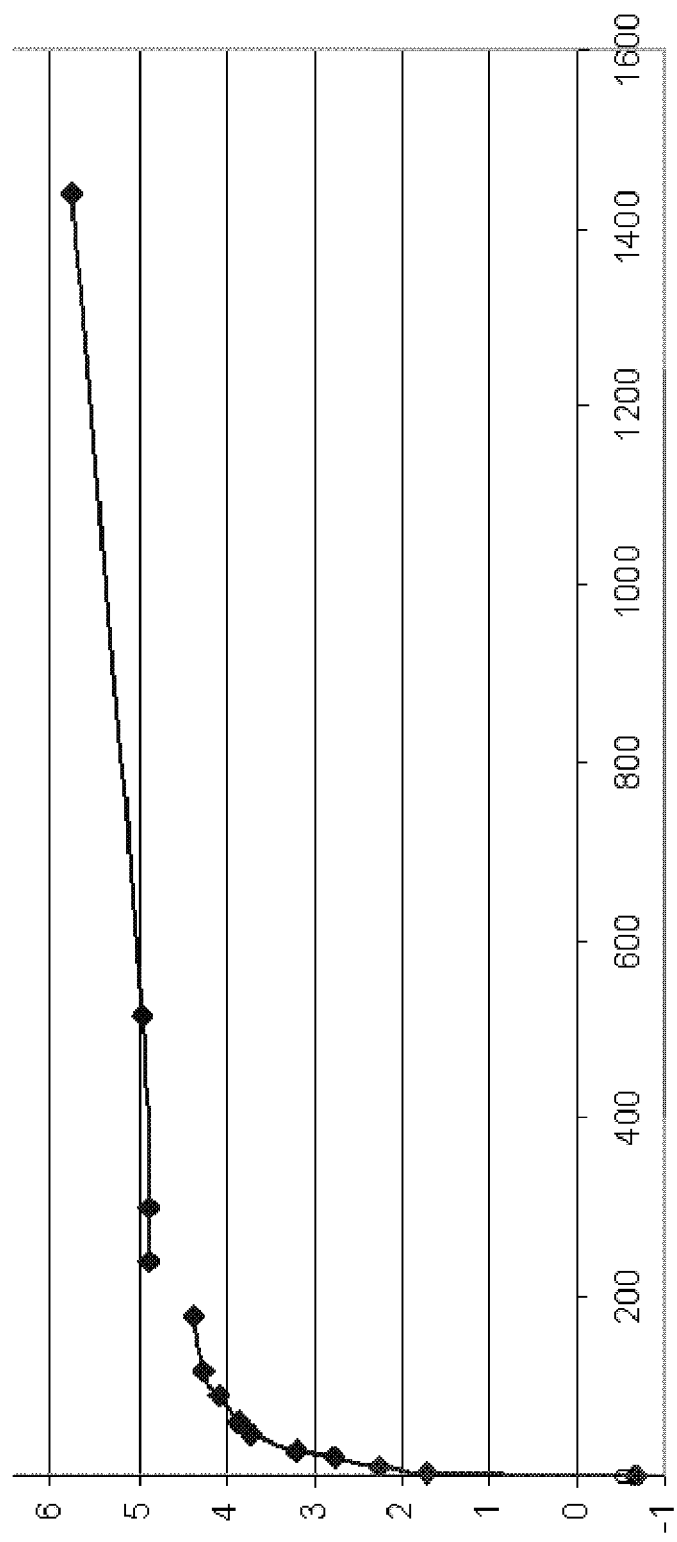
FIG. 4f Adsorption isotherm of 20% XGO-LCH-2-hydroxypropyl trimethyl ammonium chloride to cotton fabric. Y-axis: Adsorption (mg adsorbed 20% XGO-LCH-2-hydroxypropyl trimethyl ammonium chloride/g cotton) X-axis: Time (min)

A general procedure for adsorption of polymer onto cotton fabric (IKEA Ditte). Adsorption isotherms were made for compounds, XG100kDa (FIG. 4d), 20% XGO-LCH (FIG. 4e), and 20% XGO-LCH-2-hydroxypropyl trimethyl ammonium (FIG. 4f). Adsorption after 24 hours was measured for compounds in table 4. Each compound was dissolved in deionised water, 120 mg compound into 400 ml water to give a final concentration of 0.3 mg/ml. The solutions are poured into 1 L baffled E-flasks with 12 g cotton fabric (pieces of 5 cm×5 cm) respectively. Samples are taken out from the solution at different time intervals and analyzed with brilliant red assay see example 26. The results can be seen in FIG. 4d-f and table 4. In FIG. 4d is a comparison test made with XG100kDa. In FIGS. 4e and 4f it can be seen that a higher adsorption of the modified polymers according to the present invention is obtained and it is obtained in a very short time compared to the comparison test in FIG. 4d.

TABLE 4

| Xyloglucan-Chitosan | Percent adsorbed to cotton textile after 24 hours | Xyloglucan (for comparison) | Percent adsorbed to cotton textile after 24 hours |
| --- | --- | --- | --- |
| 20% XGO-LCH-2-hydroxypropyl trimethyl ammonium chloride | 58% | XG4k | 50% |
| 20% XGO-LCH-octanoyl | 90% | XG15k | 40% |
| 20% XGO-LCH-acetyl | 95% | XG100k | 15% |
| 20% XGO-LCH | 68% | | |
| 5% XG15k-LCH | 90% | | |

Example 25

The samples from example 24 were filtered and then 200 μl of the filtered solution was mixed with 1 ml of dye (4 parts of 20% (w/v) Na2SO4 with 1 part of triiodide solution (0.5% I2+1% KI)). UV absorbance measurements were then performed at 620 nm and the amount of the desired compound adsorbed was calculated using standard curves for each specific compound see FIG. 4d, table 3.

Example 26

The Brilliant red assay solution is a mixture of 5 ml dye solution, 150 mg Cibacron Brilliant red 3B-A in 100 ml deionised water (1.5 mg/ml), and 95 ml 0.1 M glycin hydrochloride buffer.

100 μl of sample from example 23 and 24 is transferred to a cuvette and 1 ml of assay solution is added. The spectrophotometer was first calibrated with a sample with only 100 μl of water added to the cuvette followed by addition of 1 ml of assay solution. After the calibration the cuvettes with real samples was measured at 575 nm wavelength in a spectrophotometer. See FIG. 4a-c, 4e-f and table 3 and 4.

Example 27

Figure 5A:
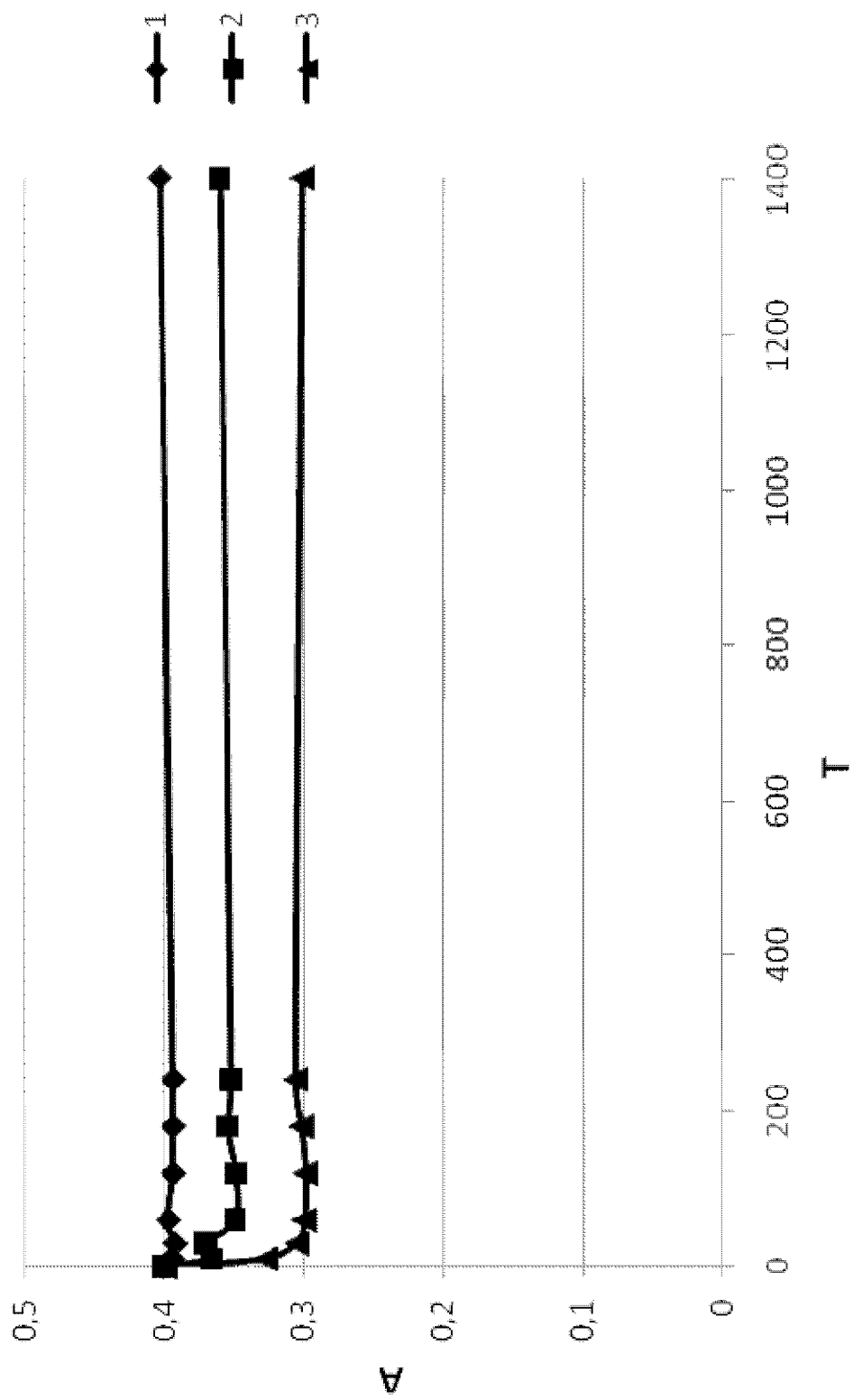
FIG. 5a Measured absorbance of metanil yellow solution (initial conc 0.05 mg/ml) from the different filter papers as a function of soak time. A=Absorbance, T=Soaking time (min), 1=Reference FP, 2=FP-20% XGO-LCH, and 3=FP-20% XGO-LCH-hydroxypropyltrimethyl ammonium chloride.
Figure 5B:
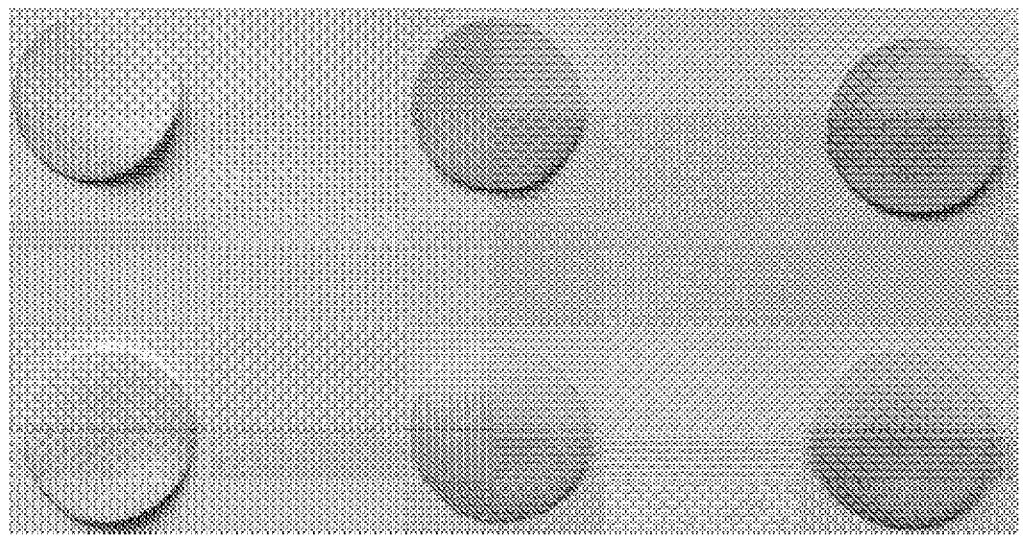
FIG. 5b Photos of dried metanil yellow dyed filter papers after 24 h in the dye solution. From left to right: Reference FP, FP-20% XGO-LCH, and FP-20% XGO-LCH-hydroxypropyltrimethyl ammonium chloride. Two different concentrations of the metanil yellow solution were used: top row 0.05 mg/ml and bottom row 0.1 mg/ml.

Filter papers (FP) (Whatman nr. 1, φ1.5 cm) were treated with 20% XGO-LCH (from example 3) and 20% XGO-LCH-hydroxypropyltrimethyl ammonium chloride (from example 19) by immersing the FP for 24 h in a 1 wt % solution of 20% XGO-LCH and 20% XGO-LCH-hydroxypropyltrimethyl ammonium chloride, respectively. The treated filter papers (FP-20% XGO-LCH and FP-20% XGO-LCH-hydroxypropyltrimethyl ammonium chloride) were thoroughly washed with distilled water for 3 days before dried in an oven at 50° C. The incorporation of positively charged R-groups onto the FP were investigated by soaking a untreated reference FP and the treated FPs in a solution of negatively charged dye, metanil yellow solution (conc. 0.1 mg/ml or 0.05 mg/ml). The dyeing of FPs was followed during 24 h by taking samples from the metanil yellow solution and thereafter the absorbance using a UV-spectrophotometer ($\lambda$420 nm) was measured. After 24 h, the metanil yellow solutions were removed and the papers were rinsed with distilled water before dried. The results are seen in FIG. 5a. In FIG. 5a it can be seen that the paper treated with 20% XGO-LCH and 20% XGO-LCH-hydroxypropyltrimethyl ammonium chloride adsorbed the negatively charge dye since a decrease in absorbance of the metanil yellow solution can be observed. Further, in FIG. 5b it can be seen that the reference paper did not get as stained as the paper treated with polymer and polymer with R-group containing positive charge.

Example 28

Figure 6:
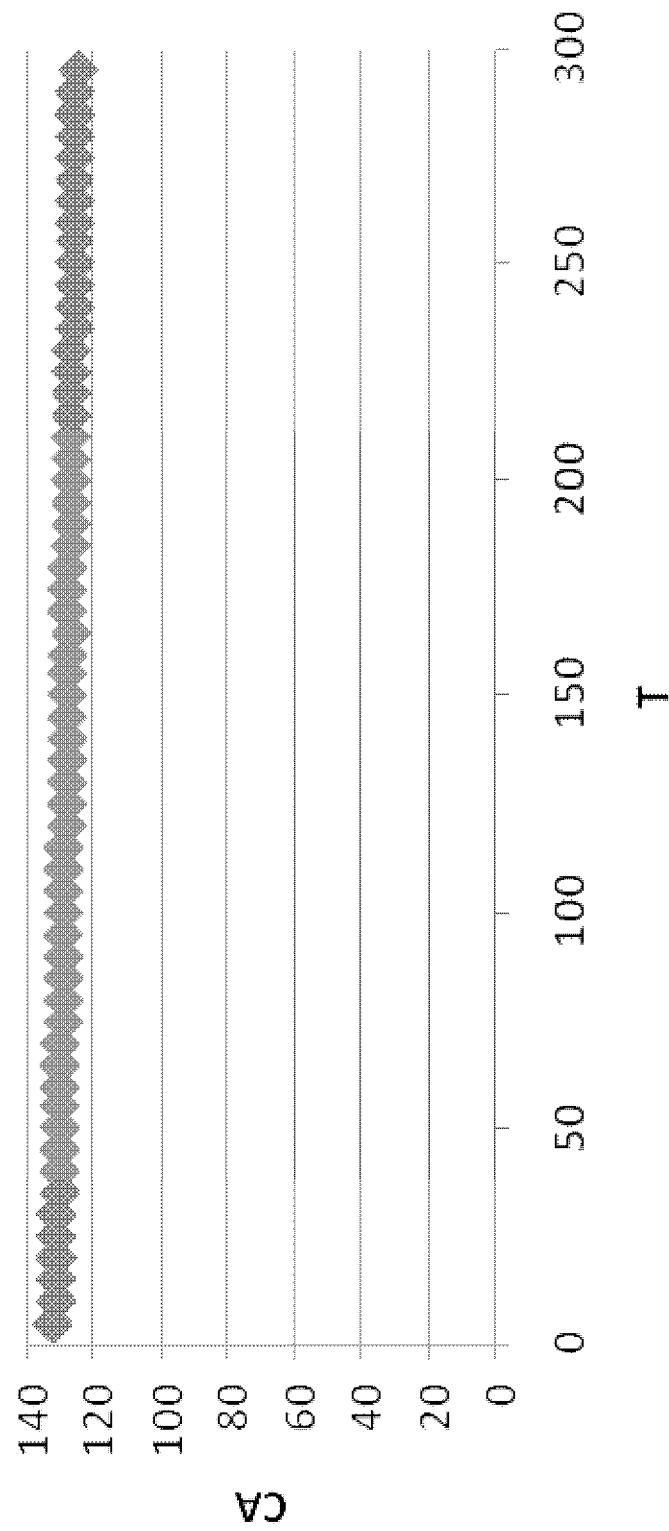
FIG. 6 Measured static contact angle on cotton with 20% XGO-LCH adsorbed to the cotton. CA=Static Contact Angle) (°), T=Time (s)

The static contact angle measurement was conducted on a KSV instrument CAM 200 equipped with a Basler A602f camera, using 3 μL droplets of MilliQ water. The contact angles were determined using the CAM software. The static contact angles were estimated as a function of time from 0 to 300 seconds. The static contact angle was measured on cotton fabric from example 24 with the compound 20% XGO-LCH adsorbed to the cotton fabric, see also FIG. 4e. The results are shown in FIG. 6. An improved hydrophobic surface is obtained, as can be seen with the static contact angle in FIG. 6. Thus, the compound 20% XGO-LCH was adsorbed very well to cotton fabric.

It can be mentioned that no reference tests could be made for textile fabrics which were untreated, since the droplets put on an untreated fabric were immediately absorbed into the fabric. It is thus not possible to measure a contact angle on untreated fabrics.

The invention claimed is:

1. A polymer made of a primary amine functionalized polymer and a hemicellulose, wherein the primary amine functionalized polymer is covalently bound to the reducing end of the hemicellulose, wherein the polymer and the hemicellulose are connected via reductive amination or the polymer and the hemicellulose are connected by an imine bond between the amino groups of the primary amine functionalized polymer and the reducing end of the hemicellulose, and wherein the hemicellulose has a molecular weight of at least 1 kDa.

2. A polymer according to claim 1, wherein the primary amine functionalized polymer and the hemicellulose are bound to each other by reductive amination between free amino groups of the primary amine functionalized polymer and the reducing end of the hemicellulose.

3. A polymer according to claim 1, wherein the primary amine functionalized polymer and the hemicellulose are bound to each other by an imine bond between the amino groups of the primary amine functionalized polymer and the reducing end of the hemicellulose.

4. A polymer according to claim 1, wherein the hemicellulose is selected from the group comprising xylan, arabinoxylan, glucuronoxylan, glucuronoarabinoxylan, glucomannan, galactomannan, galactoglucomannan, and xyloglucan or a combination thereof.

5. A polymer according to claim 1, wherein the primary amine functionalized polymer are selected from the group of homo- or co-polymers comprising polyallylamine, polyvinylamine, poly(vinylamine-co-vinylformamide, poly(ethyleneimine), and chitosan or a combination thereof.

6. A polymer according to claim 1, wherein the hemicellulose has a molecular weight of 1 kDa to 2000 kDa.

7. A polymer according to claim 1, wherein the primary amine functionalized polymer has a molecular weight of more than 100 Da.

8. A polymer according to claim 1, wherein at least one functional group R is bonded to at least one amine group and/or hydroxyl group of the polymer, wherein R is selected from the group ionic groups, hydrophobic groups, uncharged hydrophilic groups, groups containing electrophilic atoms, nucleophiles, enzymatically reactive groups, monomers for polymerisation reactions and/or curing, chromophoric or fluorophoric groups, radioactive isotopes, free-radical precursors and stable free radical moieties, nucleic acid sequences, amino acid sequences, proteins or protein-binding agents, receptors, hormones, vitamins, drugs, firming agent, UV absorbers, antisoiling agents, stain release agents, non-redepositioning agent, dye molecules, radioactive groups, perfumes, enzymes, oil repellent agents, water repellent agents, soil release agents, soil repellent agents, dyes including fabric renewing dyes, hueing dyes, dye intermediates, dye fixatives, lubricants, antisperm agent, fabric softeners, photofading inhibitors, antiwrinkle/ironing agents, shape retention agents, sunscreens, antioxidants, crease resistant agents, antimicrobial agents, skin benefit agents, anti-fungal agents, antibacterial agents, insect repellents, photobleaches, photoinitiators, enzyme inhibitors, bleach catalysts, odor neutralizing agents, pheromones, fluorescent brighteners, and mixtures thereof.

9. A polymer according to claim 1, wherein at least one functional group R is bonded via a linking group to at least one amine group and/or hydroxyl group of the polymer wherein R is selected from the group of ionic groups, hydrophobic groups, uncharged hydrophilic groups, groups containing electrophilic atoms, nucleophiles, enzymatically reactive groups, monomers for polymerisation reactions and/or curing, chromophoric or fluorophoric groups, radioactive isotopes, free-radical precursors and stable free radical moieties, nucleic acid sequences, amino acid sequences, proteins or protein-binding agents, receptors, hormones, vitamins, drugs, firming agent, UV absorbers, antisoiling agents, stain release agents, non-redepositioning agent, dye molecules, radioactive groups, perfumes, enzymes, oil repellent agents, water repellent agents, soil release agents, soil repellent agents, dyes including fabric renewing dyes, hueing dyes, dye intermediates, dye fixatives, lubricants, antisperm agent, fabric softeners, photofading inhibitors, antiwrinkle/ironing agents, shape retention agents, sunscreens, antioxidants, crease resistant agents, antimicrobial agents, skin benefit agents, anti-fungal agents, antibacterial agents, insect repellents, photobleaches, photoinitiators, enzyme inhibitors, bleach catalysts, odor neutralizing agents, pheromones, fluorescent brighteners, and mixtures thereof.

10. A composition for treatment of a cellulose material, wherein the composition comprises the polymer according to claim 1.

11. A composition comprising the polymer according to claim 1, wherein the composition is a detergent composition.

12. A cross-linking agent composition comprising the polymer according to claim 1.

13. A method of treating a cellulose material, comprising contacting a cellulose material with the composition according to claim 10.

14. A method according to claim 13, wherein the cellulose material is selected from the group of wood, paper, pulp, paperboard, filter papers, fine papers, banknote paper, newsprint, liner boards, tissue and other hygiene products, sack, kraft papers, textile, cellulosic membranes, and mixtures thereof.

15. A method according to claim 13, wherein the cellulose in the cellulose material originates from wood, cellulose, plants, cotton, linen, hemp, flax, viscose, regenerated cellulose, product of cellulose derivatives, ramie, bacteria, algae, or any other non-wood based cellulose and mixtures thereof.

16. A method according to claim 13, wherein the cellulose material is in the form of wood, cellulose nanofibres nanowhiskers, microfibrillated cellulose, fibres, threads or fabrics.

17. A method according to claim 16, wherein the fabric is a nonwoven fabric or a woven fabric.

18. A method according to claim 13, wherein the cellulose material is paper, pulp or cellulose fabrics.

* * * * *